(12) United States Patent
Cameron

(10) Patent No.: US 10,729,503 B2
(45) Date of Patent: Aug. 4, 2020

(54) INSTRUMENT COLLISION DETECTION AND FEEDBACK

(71) Applicant: TITAN MEDICAL INC., Toronto, Ontario (CA)

(72) Inventor: Peter Cameron, Menlo Park, CA (US)

(73) Assignee: Titan Medical Inc., Toronto, Ontario (CA)

( * ) Notice: Subject to any disclaimer, the term of this patent is extended or adjusted under 35 U.S.C. 154(b) by 366 days.

(21) Appl. No.: 15/570,286

(22) PCT Filed: Dec. 15, 2015

(86) PCT No.: PCT/CA2015/000600
§ 371 (c)(1),
(2) Date: Oct. 27, 2017

(87) PCT Pub. No.: WO2016/176755
PCT Pub. Date: Nov. 10, 2016

(65) Prior Publication Data
US 2018/0132956 A1    May 17, 2018

Related U.S. Application Data

(60) Provisional application No. 62/156,049, filed on May 1, 2015.

(51) Int. Cl.
*A61B 34/37*    (2016.01)
*G05B 19/4061*    (2006.01)
(Continued)

(52) U.S. Cl.
CPC .............. *A61B 34/37* (2016.02); *A61B 34/74* (2016.02); *A61B 34/76* (2016.02); *B25J 9/1676* (2013.01);
(Continued)

(58) Field of Classification Search
CPC combination set(s) only.
See application file for complete search history.

(56) References Cited

U.S. PATENT DOCUMENTS 4,578,757 A * 3/1986 Stark ...................... A61B 6/102
250/363.02
5,347,459 A    9/1994 Greenspan et al.
(Continued)

FOREIGN PATENT DOCUMENTS

| CA | 2 635 135 | 8/2007 |
|---|---|---|
| CA | 2 879 414 | 2/2014 |
| WO | WO 2009/158164 | 12/2009 |

OTHER PUBLICATIONS

International Search Report and Written Opinion in PCT Application No. PCT/CA2015/000600, dated Apr. 14, 2016 in 11 pages.
(Continued)

*Primary Examiner* — Spencer D Patton
(74) *Attorney, Agent, or Firm* — Knobbe, Martens, Olson & Bear LLP

(57) ABSTRACT

A method of operating a robotic control system comprising a master apparatus in communication with a plurality of input devices having respective handles capable of translational and rotational movement and a slave system having a tool positioning device corresponding to each respective handle and holding a respective tool having an end effector whose position and orientation is determined in response to a position and orientation of a corresponding handle. The method involves producing desired new end effector positions and orientations of respective end effectors in response to current positions and orientations of corresponding handles, using the desired new end effector positions and orientations to determine distances from each point of a first plurality of points along a first tool positioning device to each point of a plurality of points along at least one other
(Continued)

tool positioning device, and determining and notifying that any of the distances meets a proximity criterion.

19 Claims, 13 Drawing Sheets

(51) Int. Cl.
   *B25J 9/16* (2006.01)
   *B25J 13/02* (2006.01)
   *A61B 34/00* (2016.01)
   *A61B 17/00* (2006.01)
   *A61B 34/10* (2016.01)

(52) U.S. Cl.
   CPC .......... *B25J 9/1689* (2013.01); *B25J 13/025* (2013.01); *G05B 19/4061* (2013.01); *A61B 2017/00115* (2013.01); *A61B 2017/00119* (2013.01); *A61B 2017/00123* (2013.01); *A61B 2034/102* (2016.02); *G05B 2219/39135* (2013.01); *G05B 2219/49157* (2013.01)

(56) References Cited

U.S. PATENT DOCUMENTS

| | | | |
|---|---|---|---|
| 9,333,650 B2* | 5/2016 | Bajo | .................. B25J 9/163 |
| 2003/0109780 A1* | 6/2003 | Coste-Maniere | ...... B25J 9/1671 |
| | | | 600/407 |
| 2003/0225479 A1 | 12/2003 | Waled | |
| 2008/0234864 A1 | 9/2008 | Sugiura et al. | |
| 2009/0192524 A1 | 7/2009 | Itkowitz et al. | |
| 2013/0325030 A1 | 12/2013 | Hourtash et al. | |
| 2013/0343640 A1* | 12/2013 | Buehler | ................ B25J 9/0087 |
| | | | 382/155 |
| 2014/0142593 A1 | 5/2014 | Fielding et al. | |
| 2014/0277741 A1 | 9/2014 | Kwon et al. | |

OTHER PUBLICATIONS

Extended European Search Report in Application No. 15891039.8, dated Mar. 22, 2018.

* cited by examiner

INSTRUMENT COLLISION DETECTION AND FEEDBACK

CROSS-REFERENCE TO RELATED APPLICATION

This application is a U.S. National Phase Application under 35 U.S.C. § 371 of International Application No. PCT/CA2015/000600 filed on Dec. 15, 2015 and published as WO 2016/176755 A1 on Nov. 10, 2016, which claims the benefit of priority from U.S. Provisional Application No. 62/156,049, filed May 1, 2015. The entire disclosures of all of the above applications are incorporated herein by reference.

BACKGROUND

1. Field

This disclosure relates to master-slave robotic systems such as those used for laparoscopic surgery and more particularly to prevention of collision of surgical tools and/or robotic manipulators during surgery.

2. Description of Related Art

When a plurality of dexterous tools are deployed in close proximity, instances can arise when instruments physically contact one another. There may be portions of the dexterous tools that are not intended to contact each other. Contact of the tools at points on a dexterous section thereof can cause unintended or unexpected motion of end effectors coupled to the dexterous tools. For example, the tools may become caught on one another and may flick when freed, resulting in a sudden and/or unexpected movement of the tools.

SUMMARY

The disclosure describes a method of operating a robotic control system comprising a master apparatus in communication with a plurality of input devices having respective handles capable of translational and rotational movement and a slave system having a tool positioning device corresponding to each respective handle, each tool positioning device holding a respective tool having an end effector whose position and orientation is determined in response to a position and orientation of a corresponding handle. The method involves causing at least one processor circuit associated with the master apparatus to produce desired new end effector positions and desired new end effector orientations of respective end effectors, in response to current positions and current orientations of corresponding respective handles. The method further involves causing the at least one processor circuit to use the desired new end effector positions and orientations to determine distances from each point of a first plurality of points along a first tool positioning device to each point of a plurality of points along at least one other tool positioning device and causing the at least one processor circuit to determine whether any of the distances meets a proximity criterion. The method further involves causing the at least one processor circuit to notify an operator, of the handles associated with tool positioning devices associated with distance that meets the proximity criterion, to indicate that the proximity criterion has been met.

Causing the at least one processor circuit to notify the operator may involve causing the at least one processor circuit to signal the input devices associated with the handles associated with the tool positioning devices associated with the distance that meets the proximity criterion, to cause the handles associated with the tool positioning devices associated with the distance that meets the proximity criterion to present haptic feedback to the operator, the haptic feedback impeding movement of the handles in a direction that would shorten the distance that meets the proximity criterion.

Causing the at least one processor circuit to notify the operator may involve causing the at least one processor circuit to produce annunciation signals for causing an annunciator to annunciate that the proximity criterion has been met.

Causing the at least one processor circuit to produce annunciation signals may involve causing the at least one processor circuit to produce display control signals for causing a display to depict a visual representation indicative of the distance that meets the proximity criterion.

Causing the at least one processor circuit to produce annunciation signals may involve causing the at least one processor circuit to produce audio control signals for causing an audio device to provide an audible sound indicative of the distance that meets the proximity criterion.

The method may further involve causing the at least one processor circuit to disable movement of all tool positioning devices associated with the distance that meets the proximity criterion.

Causing the at least one processor circuit to disable movement of all positioning devices associated with the distance that meets the proximity criterion may involve causing the at least one processor circuit to transmit control signals to respective slave systems associated with the positioning devices associated with the distance, each control signal identifying a current end effector position and orientation based on a current position and orientation of the corresponding handle when the proximity criterion is not met, and causing the at least one processor circuit to cause the control signals transmitted to the slave systems associated with the tool positioning devices associated with the distance that meets the proximity criterion to identify a previous position and orientation of respective associated end effectors when the proximity criterion is met.

The method may involve causing the at least one processor circuit to enable movement of the tool positioning devices associated with the distance that met the proximity criterion when the proximity criterion is no longer met.

Producing the desired new end effector position and desired new end effector orientation may include causing the at least one processor circuit to receive from each input device current handle position signals ($F_{MCURR}$) and current handle orientation signals ($R_{MCURR}$) representing a current position and a current orientation respectively of the handle of the corresponding input device, and causing the at least one processor circuit to produce, for corresponding tool positioning devices, new end effector position signals ($F_{EENEW}$) and new end effector orientation signals ($R_{EENEW}$) defining the desired new end effector position and the desired new end effector orientation, respectively of the end effector, in response to corresponding the current handle position signals ($F_{MCURR}$) and the current handle orientation signals ($R_{MCURR}$).

Causing the at least one processor circuit to receive the current handle position signals and the current handle orientation signals may involve causing the at least one processor circuit to periodically receive the current handle position signals and the current handle orientation signals.

The method may involve causing the at least one processor circuit to receive an enablement signal controlled by the operator, and causing the at least one processor circuit to detect a change in state of the enablement signal and when the change is detected store the current handle position signals ($\vec{F}_{MCURR}$) and the current handle orientation signals ($R_{MCURR}$) as master base position signals ($\vec{F}_{MBAS}$) and master base orientation signals ($R_{MBASE}$) respectively, and store the new end effector position signals ($\vec{F}_{EENEW}$) and the new end effector orientation signals ($R_{EENEW}$) as end effector base position signals ($\vec{F}_{EEBASE}$) and end effector base orientation signals ($R_{EEBASE}$) respectively.

Causing the master apparatus to produce the new end effector position signals ($\vec{F}_{EENEW}$) and the new end effector orientation signals ($R_{EENEW}$) may involve the master apparatus to compute the new end effector position signals and the new end effector orientation signals according to the following relations:

$$\vec{F}_{EENEW} = A(\vec{F}_{MCURR} - \vec{F}_{MBAS}) + \vec{F}_{EEBASE}; \text{ and}$$

$$R_{EENEW} = R_{EEBASE} R_{MBASE}^{-1} R_{MCURR}$$

Each of the tool positioning devices may involve a plurality of segments each comprised of a plurality of vertebrae and at least some of the points in each of the plurality of points may be points on a respective segment or a vertebrae of a segment.

The method may involve, for each tool positioning device, causing the at least one processor circuit to compute vectors from a reference point associated with the tool positioning device to a point on a segment of the tool positioning device, based on the desired new end effector position and orientation calculated for the end effector associated with the tool positioning device.

The method may involve causing the at least one processor circuit to compute a position of at least one vertebrae associated with the segment, based on the position of the point on the segment.

The disclosure further describes a non-transitory computer readable medium encoded with codes for directing a processor circuit to execute any of the methods described above.

The disclosure further describes an apparatus for use in a robotic control system, the apparatus in communication with a plurality of input devices having respective handles capable of translational and rotational movement and the robotic control system comprising a slave system having a tool positioning device corresponding to each respective handle, each tool positioning device holding a respective tool having an end effector whose position and orientation is determined in response to a position and orientation of a corresponding handle. The apparatus includes means for producing desired new end effector positions and desired new end effector orientations of respective end effectors, in response to current positions and current orientations of corresponding respective handles, and means for determining distances from each point of a first plurality of points along a first tool positioning device, to each point of a plurality of points along at least one other tool positioning device based on the desired new end effector positions and orientations. The apparatus further includes means for determining whether any of the distances meets a proximity criterion and means for notifying an operator, of the handles associated with tool positioning devices associated with the distance that meets the proximity criterion to indicate that the proximity criterion has been met.

The means for notifying the operator may include means for signaling the input devices associated with the handles associated with the tool positioning devices associated with the distance that meets the proximity criterion, to cause the handles associated with the tool positioning devices associated with the distance that meets the proximity criterion to present haptic feedback to the operator, the haptic feedback impeding movement of the handles in a direction that would shorten the distance that meets the proximity criterion.

The means for notifying the operator may include means for producing annunciation signals for causing an annunciator to annunciate that the proximity criterion has been met.

The means for producing annunciation signals may include causing the at least one processor circuit to produce display control signals for causing a display to depict a visual representation indicative of the distance that meets the proximity criterion.

The means for producing the annunciation signals may include means for producing audio control signals for causing an audio device to provide an audible sound indicative of the distance that meets the proximity criterion.

The apparatus may further include means for disabling movement of all tool positioning devices associated with the distance that meets the proximity criterion.

The means for disabling movement of all positioning devices associated with any distance that meets the proximity criterion may include means for transmitting control signals to respective slave systems associated with the positioning devices associated with the distance, each control signal identifying a current end effector position and orientation based on a current position and orientation of the corresponding handle when the proximity criterion is not met, and means for causing the control signals transmitted to the slave systems associated with the tool positioning devices associated with the distance that meets the proximity criterion to identify a previous position and orientation of respective associated end effectors when the proximity criterion is met.

The apparatus may include means for enabling movement of the tool positioning devices associated with the distance that met the proximity criterion when the proximity criterion is no longer met.

The means for producing the desired new end effector position and desired new end effector orientation may include means for receiving from each input device current handle position signals ($\vec{F}_{MCURR}$) and current handle orientation signals ($R_{MCURR}$) representing a current position and a current orientation respectively of the handle of the corresponding input device, and means for producing, for corresponding tool positioning devices, new end effector position signals ($\vec{F}_{EENEW}$) and new end effector orientation signals ($R_{EENEW}$) defining the desired new end effector position and the desired new end effector orientation, respectively of the end effector, in response to the corresponding current handle position signals ($\vec{F}_{MCURR}$) and the current handle orientation signals ($R_{MCURR}$).

The means for receiving the current handle position signals and the current handle orientation signals may include means for periodically receiving the current handle position signals and the current handle orientation signals.

The apparatus may include means for receiving an enablement signal controlled by the operator, means for detecting a change in state of the enablement signal, and means for storing the current handle position signals ($\vec{F}_{MCURR}$) and the current handle orientation signals ($R_{MCURR}$) as master base position signals ($\vec{F}_{MBAS}$) and master base orientation signals ($R_{MBASE}$) respectively, when the change is detected. The apparatus may further include means for storing the new end effector position signals ($\bar{F}_{EENEW}$) and the new end effector orientation signals ($R_{EENEW}$) as end effector base position signals ($\bar{F}_{EEBASE}$) and end effector base orientation signals ($R_{EEBASE}$) respectively, when the change is detected.

The means for computing the new end effector position signals ($\bar{F}_{EENEW}$) and the new end effector orientation signals ($R_{EENEW}$) may include means for computing the new end effector position signals and the new end effector orientation signals according to the following relations:

$$\bar{F}_{EENEW} = A(\bar{F}_{MCURR} - \bar{F}_{MBAS}) + \bar{F}_{EEBASE}; \text{ and}$$

$$R_{EENEW} = R_{EEBASE} R_{MBASE}^{-1} R_{MCURR}$$

Each of the tool positioning devices may include a plurality of segments each comprised of a plurality of vertebrae and at least some of the points in each the plurality of points may be points on a respective segment or a vertebrae of a segment.

The apparatus may include means for computing vectors to points along each tool positioning device from a reference point associated with the tool positioning device to a point on a segment of the tool positioning device, based on the desired new end effector position and orientation calculated for the end effector associated with the tool positioning device.

The apparatus may include means for computing a position of at least one vertebra associated with the segment, based on the position of the point on the segment.

The disclosure further describes an apparatus for use in a robotic control system, the apparatus in communication with a plurality of input devices having respective handles capable of translational and rotational movement and a slave system having a tool positioning device corresponding to each respective handle, each tool positioning device holding a respective tool having an end effector whose position and orientation is determined in response to a position and orientation of a corresponding handle. The apparatus includes at least one processor circuit configured to produce desired new end effector positions and desired new end effector orientations of respective end effectors, in response to current positions and current orientations of corresponding respective handles, and the at least one processor circuit is configured to use the desired new end effector positions and orientations to determine distances from each point of a first plurality of points along a first tool positioning device to each point of a plurality of points along at least one other tool positioning device. The apparatus further includes at least one processor circuit configured to determine whether any of the distances meets a proximity criterion, and to notify an operator, of the handles associated with tool positioning devices associated with the distance that meets the proximity criterion, to indicate that the proximity criterion has been met.

The at least one processor circuit may be configured to notify the operator by signaling the input devices associated with the handles associated with the tool positioning devices associated with the distance that meets the proximity criterion, to cause the handles associated with the tool positioning devices associated with the distance that meets the proximity criterion to present haptic feedback to the operator, the haptic feedback impeding movement of the handles in a direction that would shorten the distance that meets the proximity criterion.

The at least one processor circuit may be configured to notify the operator by producing annunciation signals for causing an annunciator to annunciate that the proximity criterion has been met.

The annunciation signals may include display control signals for causing a display to depict a visual representation indicative of the distance that meets the proximity criterion.

The annunciation signal may include audio control signals for causing an audio device to provide an audible sound indicative of the distance that meets the proximity criterion.

The at least one processor circuit may further be configured to disable movement of all tool positioning devices associated with the distance that meets the proximity criterion.

The at least one processor circuit may be configured to disable movement of all positioning devices associated with the distance that meets the proximity criterion by transmitting control signals to respective slave systems associated with the positioning devices associated with the distance, each control signal identifying a current end effector position and orientation based on a current position and orientation of the corresponding handle when the proximity criterion is not met, and causing the control signals transmitted to the slave systems associated with the tool positioning devices associated with the distance that meets the proximity criterion to identify a previous position and orientation of respective associated end effectors when the proximity criterion is met.

The at least one processor circuit may be further configured to enable movement of the tool positioning devices associated with the distance that met the proximity criterion when the proximity criterion is no longer met.

The at least one processor circuit may be configured to produce the desired new end effector position and desired new end effector orientation by receiving from each input device current handle position signals ($\bar{F}_{MCURR}$) and current handle orientation signals ($R_{MCURR}$) representing a current position and a current orientation respectively of the handle of the corresponding input device, and producing, for corresponding tool positioning devices, new end effector position signals ($\bar{F}_{EENEW}$) and new end effector orientation signals ($R_{EENEW}$) defining the desired new end effector position and the desired new end effector orientation, respectively of the end effector, in response to corresponding current handle position signals ($\bar{F}_{MCURR}$) and current handle orientation signals ($R_{MCURR}$).

The at least one processor circuit may be configured to receive the current handle position signals and the current handle orientation signals on a periodic basis.

The at least one processor circuit may be configured to receive an enablement signal controlled by the operator and to detect a change in state of the enablement signal and when the change is detected, to store the current handle position signals ($\bar{F}_{MCURR}$) and the current handle orientation signals ($R_{MCURR}$) as master base position signals ($\bar{F}_{MBAS}$) and master base orientation signals ($R_{MBASE}$) respectively, and store the new end effector position signals ($\bar{F}_{EENEW}$) and the new end effector orientation signals ($R_{EENEW}$) as end effector base position signals ($\bar{F}_{EEBASE}$) and end effector base orientation signals ($R_{EEBASE}$) respectively.

The at least one processor circuit may be configured to compute the new end effector position signals ($\bar{F}_{EENEW}$) and the new end effector orientation signals ($R_{EENEW}$) according to the following relations:

$$\bar{F}_{EENEW} = A(\bar{F}_{MCURR} - \bar{F}_{MBAS}) + \bar{F}_{EEBASE}; \text{ and}$$

$$R_{EENEW} = R_{EEBASE} R_{MBASE}^{-1} R_{MCURR}$$

Each of the tool positioning devices may include a plurality of segments each comprised of a plurality of vertebrae and at least some of the points in each the plurality of points may be points on a respective segment or a vertebrae of a segment.

The at least one processor circuit may be configured to, for each tool positioning device, compute vectors from a reference point associated with the tool positioning device to a point on a segment of the tool positioning device, based on the desired end effector position calculated for the end effector associated with the tool positioning device.

The at least one processor circuit may be configured to compute a position of at least one vertebrae associated with the segment, based on the position of the point on the segment.

Other aspects and features of the present disclosure will become apparent to those ordinarily skilled in the art upon review of the following description of specific embodiments in conjunction with the accompanying figures.

BRIEF DESCRIPTION OF THE DRAWINGS

In drawings which illustrate various embodiments described herein.

DETAILED DESCRIPTION

Figure 1:
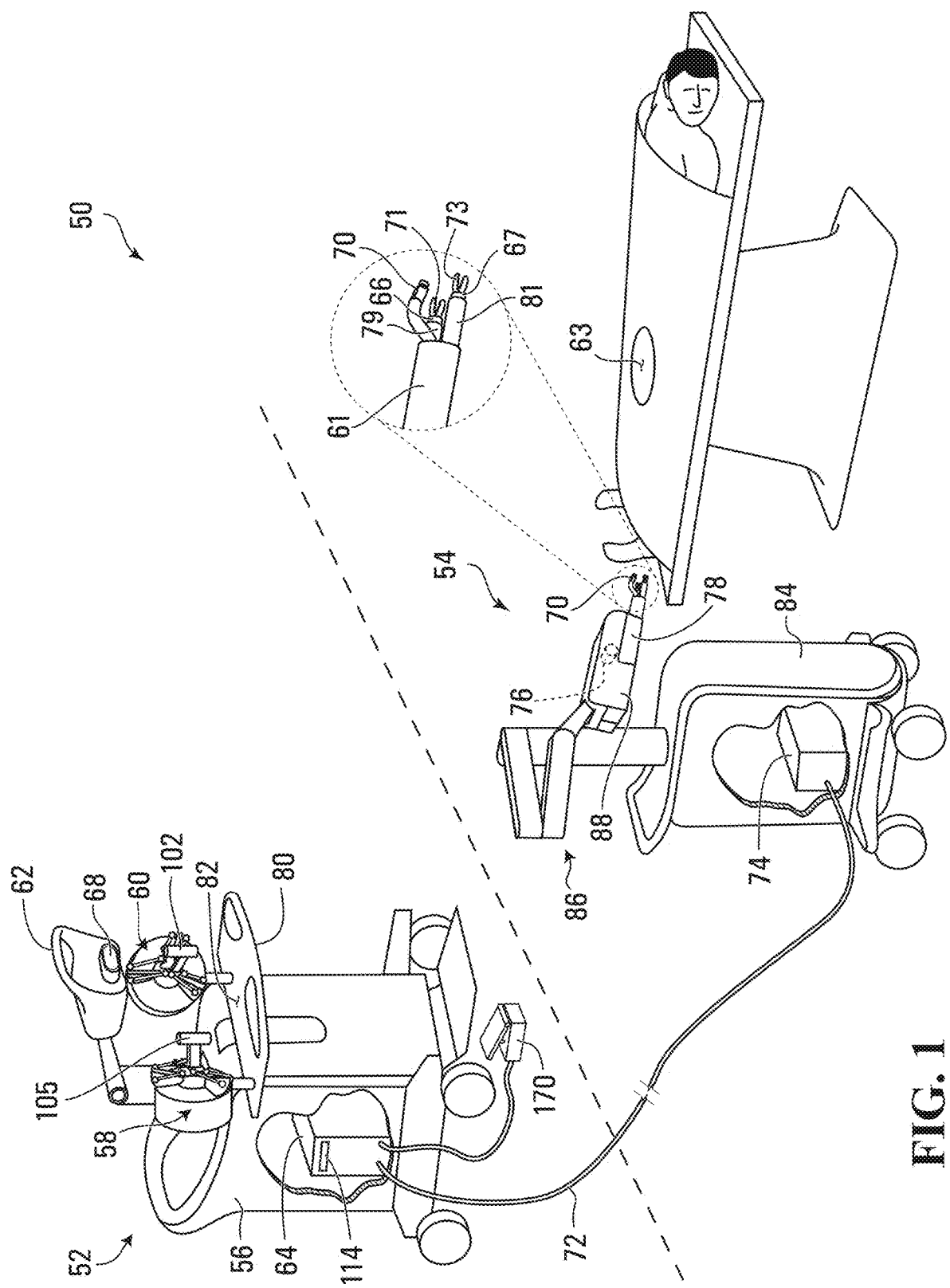
FIG. 1 is a pictorial representation of a laparoscopic surgery system according to one embodiment of the invention.

Referring to FIG. 1, a robotic control system in the form of a laparoscopic surgery system is shown generally at 50.

The system 50 includes a master subsystem 52 and a slave subsystem 54. The master subsystem 52 may be located anywhere in the world, but for the purposes of this description it will be considered to be in an operating room. The slave subsystem 54 is located in the operating room.

In the embodiment shown, the master subsystem 52 comprises a workstation 56, which in this embodiment has first and second input devices 58 and 60 and a viewer 62 in communication with a master apparatus 64 comprising at least one processor circuit. In other embodiments there may be more input devices. The first and second input devices 58 and 60 each include respective handles 105 and 102. In this embodiment the first and second input devices 58 and 60 are operable to be actuated by respective hands of an operator such as a surgeon, for example, who will perform the laparoscopic surgery by manipulating the first and second input devices of the master subsystem 52 to control corresponding tools 66 and 67 on the slave subsystem 54.

The viewer 62 may include an LCD display 68, for example, for displaying images acquired by a camera 70 on the slave subsystem 54, to enable the operator to see the tools 66 and 67 inside the patient while manipulating the first and second input devices 58 and 60 to cause the tools to move in desired ways to perform the surgery. The first and second input devices 58 and 60 produce position and orientation signals that are received by the master apparatus 64 and the master apparatus produces slave control signals that are transmitted by wires 72 or wirelessly, for example, from the master subsystem 52 to the slave subsystem 54.

The slave subsystem 54 includes a slave computer 74 that receives the slave control signals from the master subsystem 52 and produces motor control signals that control motors 76 on a drive mechanism of a tool controller 78 of the slave subsystem, to extend and retract control wires (not shown) of respective tool positioning devices 79 and 81 to position and to rotate the tools 66 and 67. Exemplary tool positioning devices and tools for this purpose are described in PCT/CA2013/001076, which is incorporated herein by reference. Generally, there will be a tool and tool positioning device associated with each of the input devices 58 and 60. In the embodiment shown the tool positioning devices 79 and 81 extend through an insertion tube 61, a portion of which is inserted through a small incision 63 in the patient, to position end effectors 71 and 73 of the tools 66 and 67 inside the patient, to facilitate the surgery.

In the embodiment shown, the workstation 56 has a support 80 having a flat surface 82 for supporting the first and second input devices 58 and 60 in positions that are comfortable to the user whose hands are actuating the first and second input devices 58 and 60.

In the embodiment shown, the slave subsystem 54 includes a cart 84 in which the slave computer 74 is located. The cart 84 has an articulated arm 86 mechanically connected thereto, with a tool holder mount 88 disposed at a distal end of the articulated arm.

Input Devices

In the embodiment shown, the first and second input devices 58 and 60 are the same, but individually adapted for left and right hand use respectively. In this embodiment, each input device 58 and 60 is an Omega.7 haptic device available from Force Dimension, of Switzerland. For simplicity, only input device 60 will be further described, it being understood that input device 58 operates in the same way.

Figure 2:
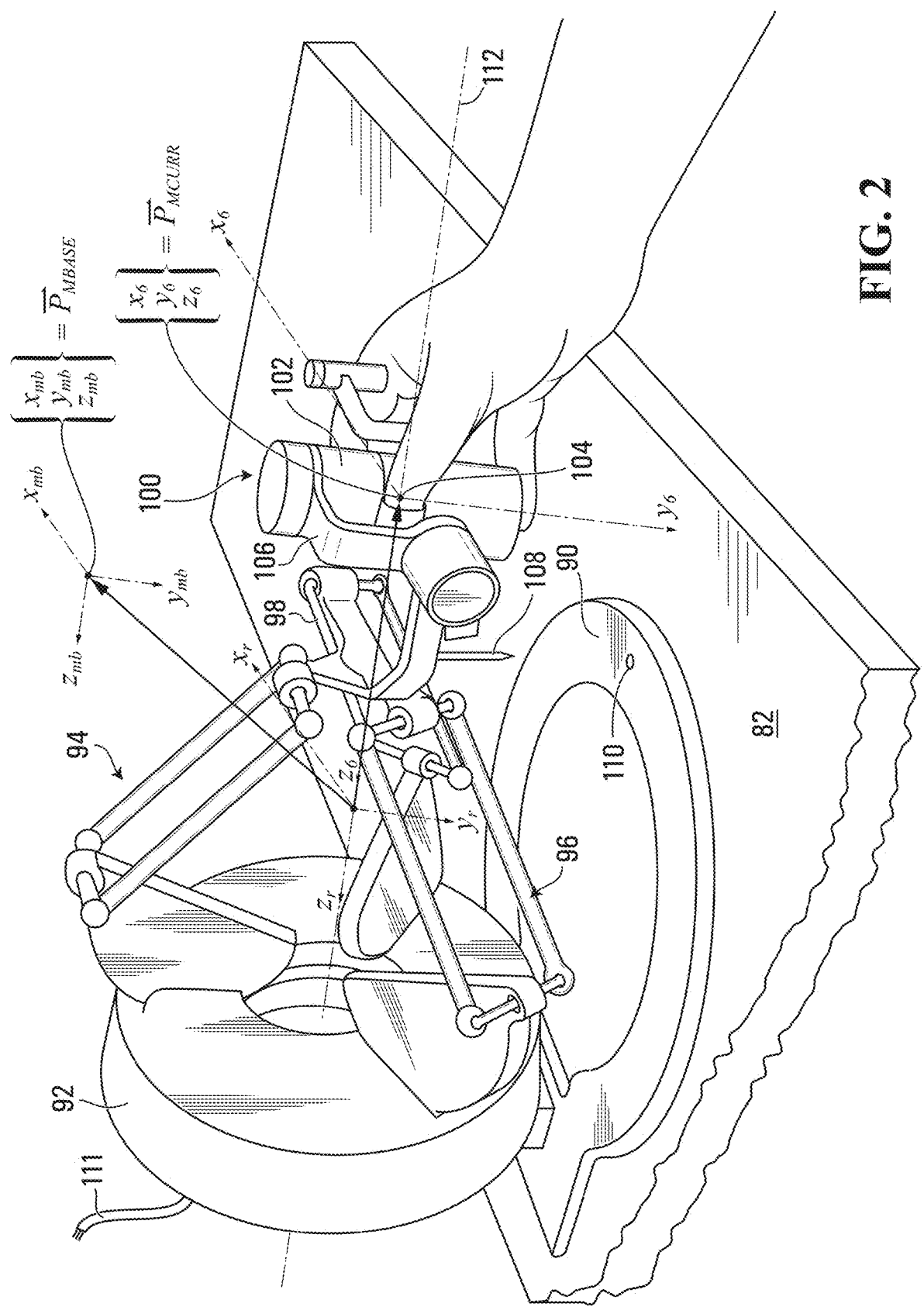
FIG. 2 is an oblique view of an input device of a master subsystem of the laparoscopic surgery system shown in FIG. 1.

Referring to FIG. 2, the input device 60 includes the flat surface 82 supports a control unit 92 having arms 94, 96, 98 connected to the handle 102, which is gimbal-mounted and can be grasped by the hand of an operator and positioned and rotated about orthogonal axes $x_6$, $y_6$ and $z_6$ of a Cartesian reference frame having an origin at a point midway along the axis of a cylinder that forms part of the handle 102. This Cartesian reference frame may be referred to as the handle reference frame and has an origin 104 (i.e. the center of the handle 102) that may be referred to as the handle position.

The arms 94, 96, 98 facilitate translational movement of the handle 102 and hence the handle position 104, in space, and confine the movement of the handle position within a volume in space. This volume may be referred to as the handle translational workspace. The control unit 92 is also able to generate a haptic force for providing haptic feedback to the handles 102 and 105 through the arms 94, 96, and 98.

The handle 102 is mounted on a gimbal mount 106 having a pin 108. The flat surface 82 has a calibration opening 110 for receiving the pin 108. When the pin 108 is received in the opening 110, the input device 60 is in a calibration position that is defined relative to a fixed master Cartesian reference frame comprising orthogonal axes $x_r$, $y_r$, $z_r$, generally in the center of the handle translational workspace. In the embodiment shown, this master reference frame has an $x_r$-$z_r$ plane parallel to the flat surface 82 and a $y_r$ axis perpendicular to the flat surface. In the embodiment shown, the $z_r$ axis is parallel to the flat surface 82 and is coincident with an axis 112 passing centrally through the control unit 92 so that pushing and pulling the handle 102 toward and away from the center of the control unit 92 along the axis 112 in a direction parallel to the flat surface 82 is a movement in the $z_r$ direction.

The control unit 92 has sensors (not shown) that sense the positions of the arms 94, 96, 98 and the rotation of the handle 102 about each of the $x_6$, $y_6$ and $z_6$ axes and produces signals representing the handle position 104 in the workspace and the rotational orientation of the handle 102 relative to the fixed master reference frame $x_r$, $y_r$, $z_r$. In this embodiment, these position and orientation signals are transmitted on wires 111 of a USB bus to the master apparatus 64. More particularly, the control unit 92 produces current handle position signals and current handle orientation signals that represent the current position and orientation of the handle 102 by a current handle position vector $\vec{F}_{MCURR}$ and a current handle rotation matrix $R_{MCURR}$, relative to the fixed master reference frame $x_r$, $y_r$, $z_r$.

For example, the current handle position vector $\vec{F}_{MCURR}$ is a vector $$\begin{Bmatrix} x_6 \\ y_6 \\ z_6 \end{Bmatrix},$$

where $x_6$, $y_6$, and $z_6$ represent coordinates of the handle position 104 within the handle translational workspace relative to the fixed master reference frame, $x_r$, $y_r$, $z_r$.

The current handle rotation matrix $R_{MCURR}$ is a 3×3 matrix $$\begin{bmatrix} x_{6x} & y_{6x} & z_{6x} \\ x_{6y} & y_{6y} & z_{6y} \\ x_{6z} & y_{6z} & z_{6z} \end{bmatrix},$$

where the columns of the matrix represent the axes of the handle reference frame $x_6$, $y_6$, $z_6$ relative to the fixed master reference frame $x_r$, $y_r$, $z_r$. $R_{MCURR}$ thus defines the current rotational orientation of the handle 102 in the handle translational workspace, relative to the $x_r$, $y_r$, $z_r$ fixed master reference frame.

Figure 3:
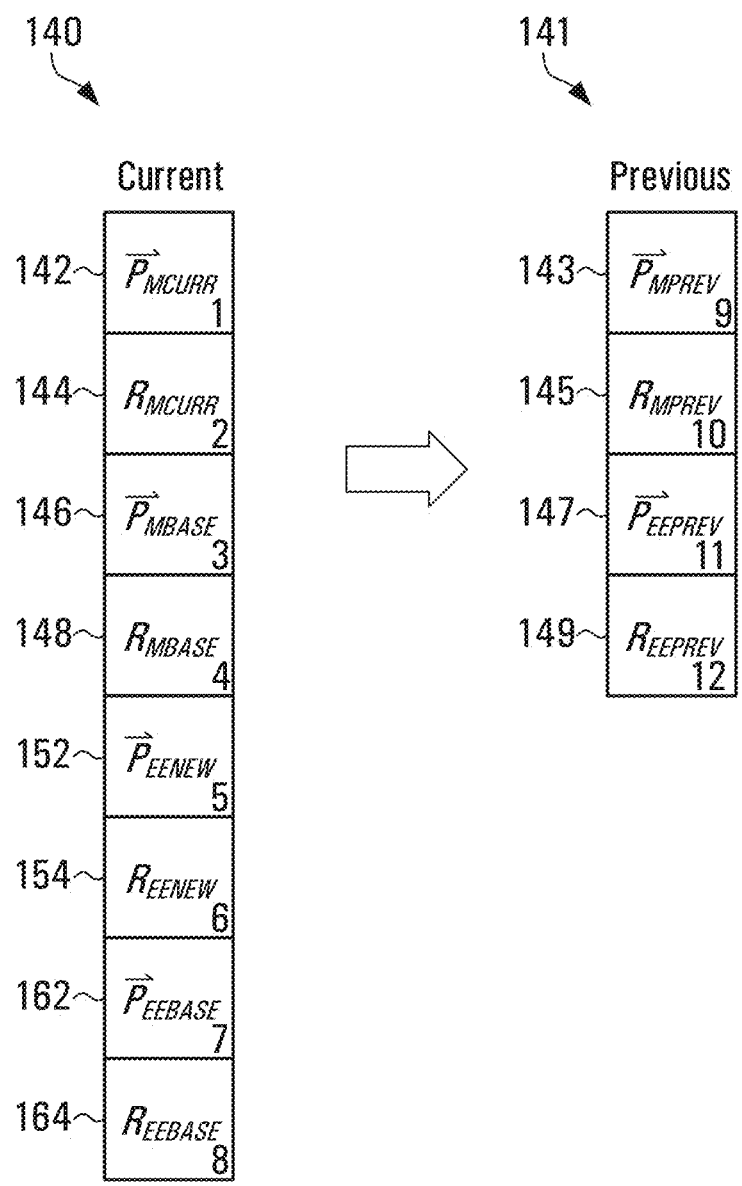
FIG. 3 is a schematic representation of current and previous value buffers maintained by a master apparatus of the system shown in FIG. 1 and updated according to the functions shown in FIG. 8.

The current handle position vector $\vec{F}_{MCURR}$ and current handle rotation matrix $R_{MCURR}$ are transmitted in the current handle position and current handle orientation signals on wires 111 of the USB bus, for example, to the master apparatus 64 in FIG. 1. Referring to FIG. 3, the master apparatus 64 includes a current memory buffer 140 that stores the current handle position vector $\vec{F}_{MCURR}$ in a first store 142 of the current buffer and stores the current handle rotation matrix $R_{MCURR}$ in a second store 144 of the current buffer 140.

Tool Positioner and End Effector

Figure 4:
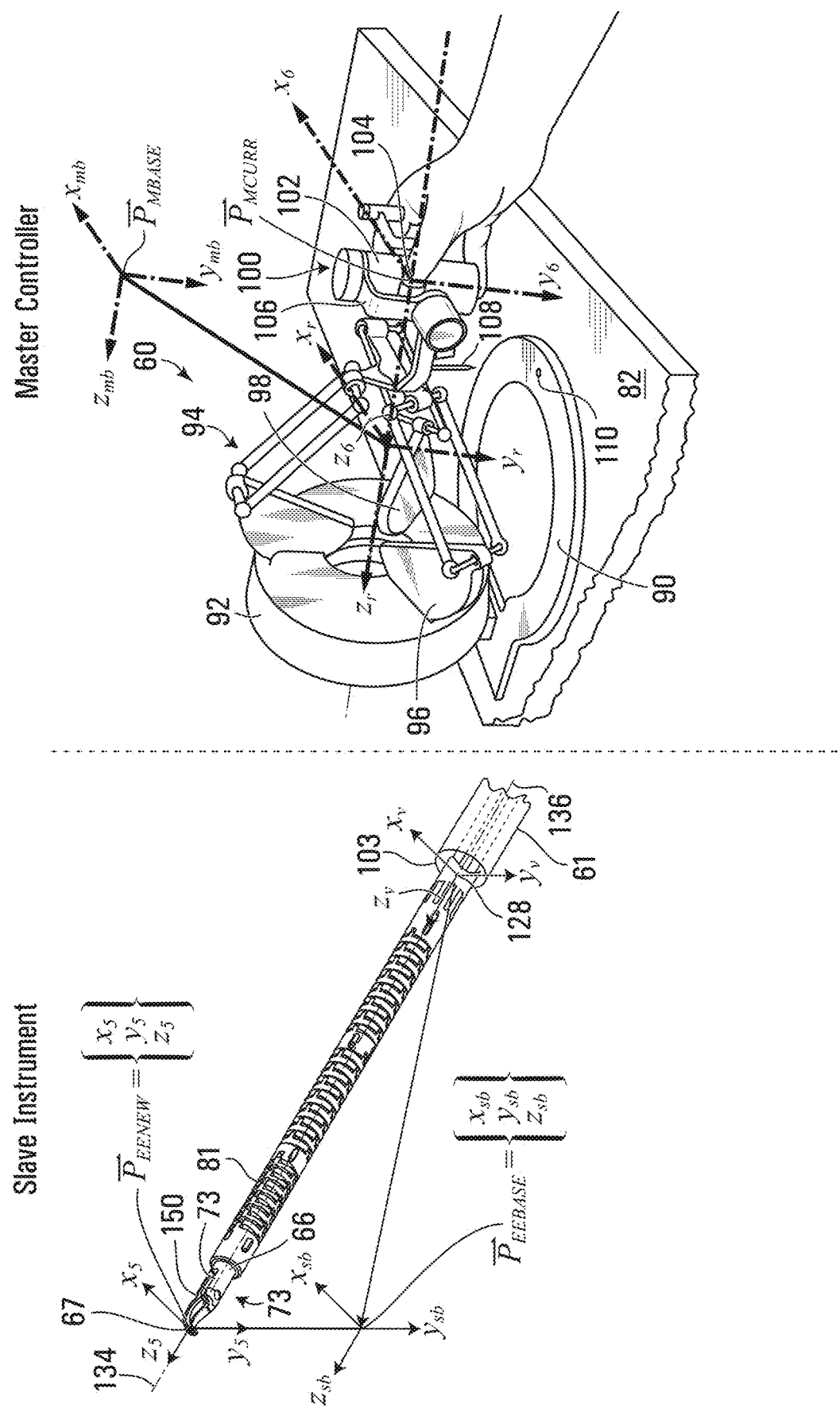
FIG. 4 is an oblique view of the input device shown in FIG. 2 and the tool positioning device of the slave subsystem shown in FIG. 1 showing relationships between base axes of the input device and the end effector.
Figure 5:
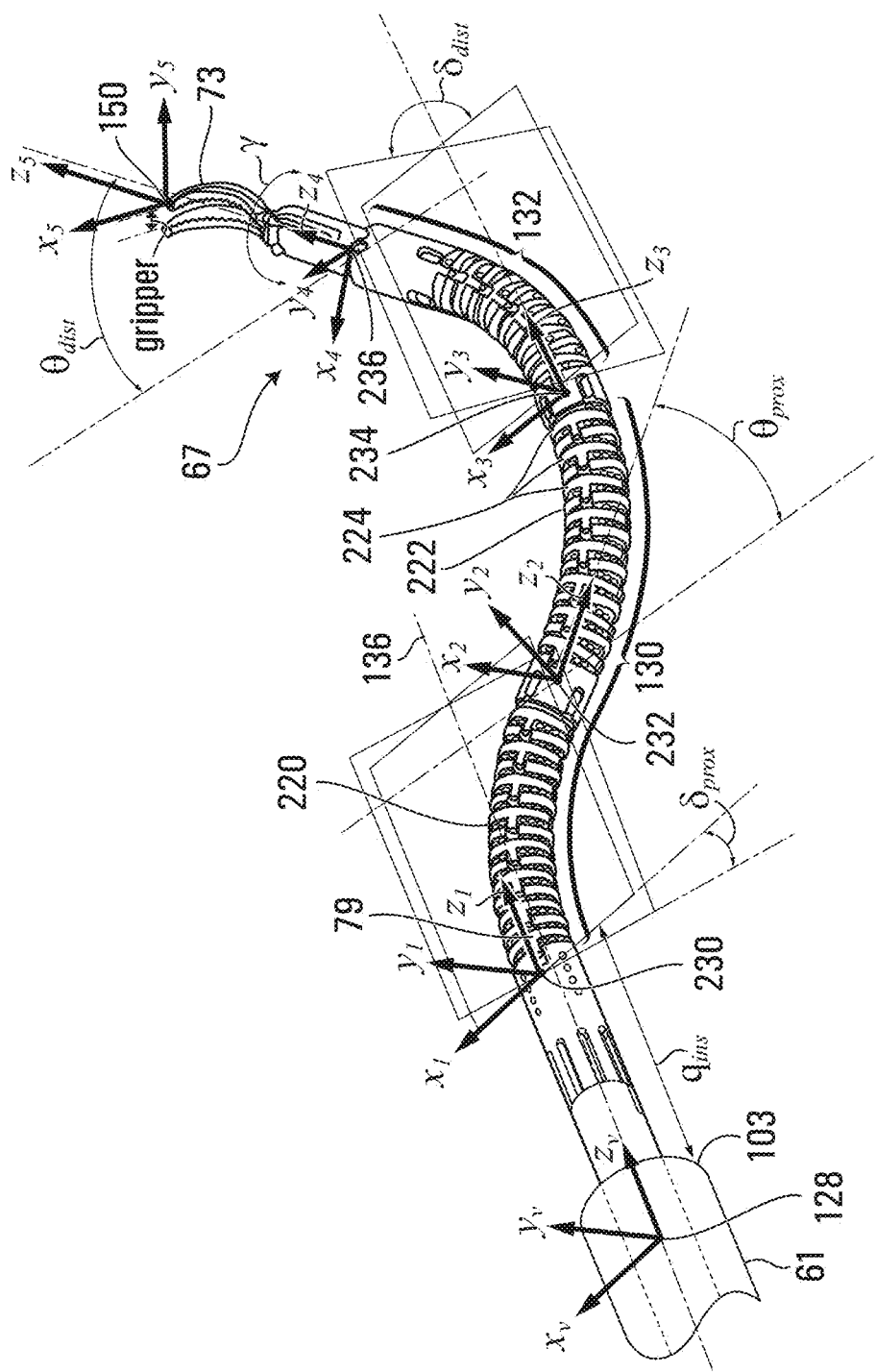
FIG. 5 is an oblique view of a tool positioning device shown in FIG. 4 with a tool in the form of an end effector held thereby, in an insertion tube of the system shown in FIG. 1.

The end effector 73 and tool positioning device 81 are further described with reference to FIG. 4 and FIG. 5. Referring to FIGS. 4 and 5 the tool positioning device 81 moves the tool 67 and its end effector 73 within a volume in space. This volume may be referred to as the end effector workspace.

The position and orientation of the end effector 73 is defined relative to a fixed slave reference frame having axes $x_v$, $y_v$ and $z_v$ which intersect at a point referred to as the fixed slave reference position 128, lying on a longitudinal axis 136 of the insertion tube 61 and contained in a plane perpendicular to the longitudinal axis 136 and containing a distal edge 103 of the insertion tube 61. The $z_v$ axis is coincident with the longitudinal axis 136 of the insertion tube 61. The $x_v$-$z_v$ plane thus contains the longitudinal axis 136 of the insertion tube 61 and the $x_v$ and $y_v$ axes define a plane perpendicular to the longitudinal axis 136 of the insertion tube 61.

In the embodiment shown, the end effector 73 includes a pair of gripper jaws, which may be positioned and oriented within the end effector workspace. A tip of the gripper jaws may be designated as an end effector position and may be defined as the origin 150 of an end effector Cartesian reference frame $x_5$, $y_5$, $z_5$. The end effector position 150 is defined relative to the slave reference position 128 and may be positioned and orientated relative to the fixed slave reference frame $x_v$, $y_v$, $z_v$.

Figure 6:
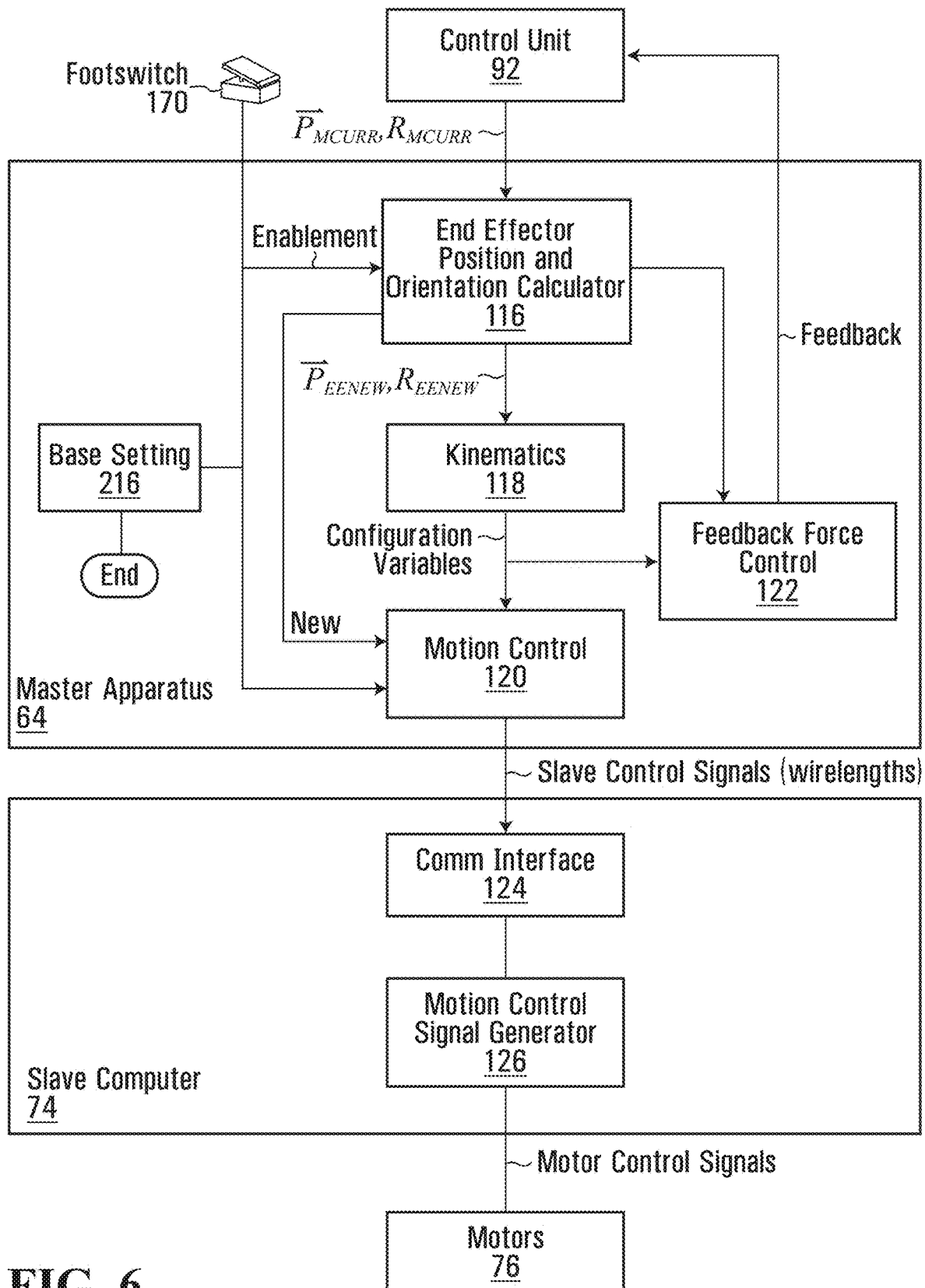
FIG. 6 is a flow chart illustrating certain functionality and certain signals produced and used by the system shown in FIG. 1.

A flow chart illustrating functions and signals produced and used by the system 50 is shown in FIG. 6. Desired new end effector positions and desired new end effector orientations are calculated as described in connection with FIG. 6, in response to the current handle position signals $\vec{F}_{MCURR}$ and current handle orientation signals $R_{MCURR}$ and are represented by a new end effector position vector $\vec{F}_{EENEW}$ and a new rotation matrix $R_{EENEW}$. For example, the new end effector position vector $\vec{F}_{EENEW}$ is a vector:

$$\begin{Bmatrix} x_5 \\ y_5 \\ z_5 \end{Bmatrix},$$

where $x_5$, $y_5$, and $z_5$ represent coordinates of the end effector position 150 within the end effector workspace relative to the $x_v$, $y_v$, $z_v$ fixed slave reference frame. The end effector rotation matrix $R_{EENEW}$ is a 3×3 matrix:

$$\begin{bmatrix} x_{5x} & y_{5x} & z_{5x} \\ x_{5y} & y_{5y} & z_{5y} \\ x_{5z} & y_{5z} & z_{5z} \end{bmatrix},$$

where the columns of the $R_{EENEW}$ matrix represent the axes of the end effector reference frame $x_5$, $y_5$, $z_5$ written in the fixed slave reference frame $x_v$, $y_v$, $z_v$. $R_{EENEW}$ thus defines a new orientation of the end effector 73 in the end effector workspace, relative to the $x_v$, $y_v$, $z_v$ fixed slave reference frame.

Footswitch

Referring back to FIG. 1, in addition to receiving signals from the input devices 58 and 60, in the embodiment shown, the master apparatus 64 is coupled to a footswitch 170 actuable by the operator (surgeon) to provide a binary enablement signal to the master apparatus 64. When the footswitch 170 is not activated, i.e. not depressed, the enablement signal is in an active state and when the footswitch 170 is depressed the enablement signal is in an inactive state. The footswitch 170 thus controls the state of the enablement signal. The enablement signal allows the operator to cause the master apparatus 64 to selectively enable and disable movement of the end effectors 71 and 73 in response to movement of the handles 105 and 102.

Master Apparatus and Slave Computer

Still referring to FIG. 1, in the embodiment shown, the master apparatus 64 is controlled by program codes stored on a non-transitory computer readable medium such as a disk drive 114. The codes direct the master apparatus 64 to perform various functions including collision detection functions. Referring to FIG. 6, these functions may be grouped into categories and expressed as functional blocks of code including a base setting block 216, an end effector position and orientation calculation block 116, a kinematics block 118, a motion control block 120, and a feedback force control block 122, each block including codes stored on the disk drive 114 of the master apparatus 64.

For ease of description, the above blocks are shown as functional blocks within the master apparatus 64 in FIG. 6. These functional blocks are executed separately but in the same manner for each input device of master subsystem 52. In the embodiment shown, there are only two input devices, 58 and 60. While the execution of these functional blocks for the input device 60, tool positioning device 81 and end effector 73 are described, it should be understood that the codes are separately executed in the same way for all other input devices, such as the input device 58, tool positioning device 79 and end effector 71 shown in FIG. 1 to achieve control of both end effectors 73 and 71 by the respective right and left hands of the operator.

The base setting block 216 is executed asynchronously, whenever the enablement signal produced by the footswitch 170 transitions from an inactive state to an active state, such as when the operator releases the footswitch in this embodiment. The base setting block 216 includes codes that direct the master apparatus 64 to set new base positions and orientations for positions and orientations of the handle 102 and end effector 73, respectively as will be described below.

Generally, the end effector position and orientation calculation block 116 includes codes that direct the master apparatus 64 to calculate new end effector position and new orientation signals, $\vec{F}_{EENEW}$ and $R_{EENEW}$, which position and orient the end effector 73 in the desired position and orientation $\vec{F}_{MCURR}$ and $R_{MCURR}$ in response to the position and orientation of the handle 102. The end effector position and orientation calculation block 116 receives the enablement signal from the footswitch 170 and produces output signals including a "new" signal and a signal that is coupled to the feedback force control block 122.

The kinematics block 118 includes codes that direct the master apparatus 64 to produce configuration variables in response to the newly calculated end effector position and orientation signals, $\vec{F}_{EENEW}$ and $R_{EENEW}$. The configuration variables define a tool positioning device pose required to position and orient the end effector 73 in the desired position and orientations.

The feedback force control block 122 includes codes that direct the master apparatus 64 to receive the configuration variables from the kinematics block 118 and to determine a theoretical location of various points along the tool positioning devices 81 and 79 in the end effector workspace, and to determine whether a distance between any two of these theoretical locations on respective tool positioning devices 81 and 79 is less than a threshold distance. When such distance is less than the threshold distance, the codes of the feedback force control block 122 direct the master apparatus 64 to cause feedback to notify the operator of the proximity.

The motion control block 120 includes codes that direct the master apparatus 64 to produce the slave control signals, in response to the configuration variables.

In the embodiment shown in FIG. 1, the slave control signals represent wire length values indicating how much certain control wires of the tool positioning device 81 of the slave subsystem 54 must be extended or retracted to cause the end effector 73 of the tool 67 to assume a desired position and orientation defined by positioning and rotating the input device 60. The slave control signals representing the control wire length values are transmitted to the slave computer 74, which has its own computer readable medium encoded with a communication interface block 124 which includes codes for directing the slave computer to receive the slave control signals from the master apparatus 64. The computer readable medium at the slave computer is also encoded with a motor control signal generator block 126 which includes codes for causing the slave computer 74 to generate motor control signals for controlling the motors 76 on the tool controller 78 to extend and retract the control wires controlling the attached tool positioning device 81 according to the control wire length values represented by the slave control signals from the master apparatus 64. The various blocks in FIG. 6 are described below in greater detail.

Base Setting Block

Figure 7:
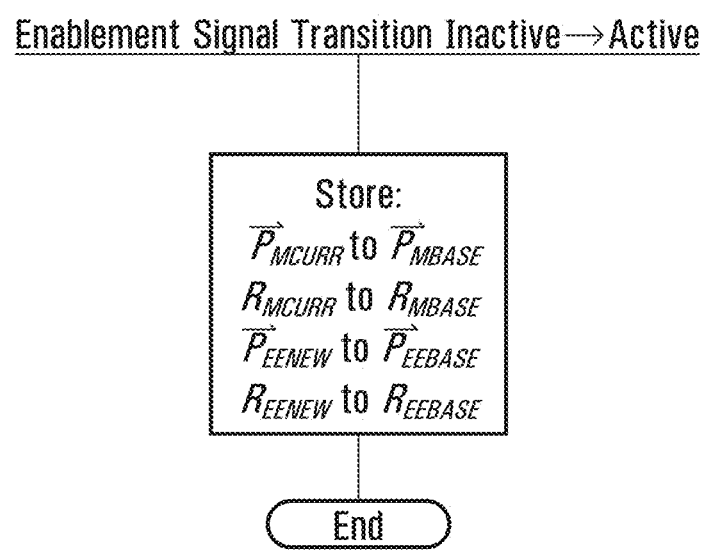
FIG. 7 is a flow chart of a storage routine executed by the master apparatus in response to detection of a signal transition of an enablement signal produced in response to user input.

A flow chart showing details of operations included in the base setting block 216 is shown in FIG. 7. Referring to FIG. 7, as disclosed above, the base setting block 216 is executed asynchronously, whenever the enablement signal transitions from an inactive state to an active state. The base setting block 216 directs the master apparatus 64 to set new base positions and new base orientations for positions and orientations of the handle 102 and end effector 73, respectively. Referring back to FIG. 3, the master apparatus 64 stores values $x_{mb}$, $y_{mb}$, $z_{mb}$ representing a definable master base position vector represented by a base position signal $\vec{F}_{MBASE}$ in a third store 146 and stores values representing a definable master base rotation matrix represented by a base orientation signal $R_{MBASE}$ in a fourth store 148.

On startup of the system 50 the master apparatus 64 initially causes the definable master base position vector $\vec{F}_{MBASE}$ to be set equal to the current handle position vector $\vec{F}_{MCURR}$ and causes the definable master base rotation matrix $R_{MBASE}$ to define an orientation that is the same as the current orientation defined by the handle rotation matrix $R_{MCURR}$ associated with the current handle rotation.

Initially, therefore:

$$\vec{F}_{MBASE} = \vec{F}_{MCURR}; \text{ and}$$

$$R_{MBASE} = R_{MCURR}$$

In other words, a definable master base reference frame represented by the axes $x_{mb}$, $y_{mb}$ and $z_{mb}$ and the handle reference frame represented by the axes $x_6$, $y_6$ and $z_6$ coincide at startup.

Thereafter, the master base position vector $\bar{F}_{MBASE}$ and the master base rotation matrix $R_{MBASE}$ are maintained at the same values as on startup until the enablement signal is activated, such as by the release of the footswitch (170 in FIG. 1), which causes the enablement signal to transition from the inactive state to the active state. In response to the inactive to active state transition of the enablement signal, the base setting block 216 in FIGS. 6 and 7 is executed to change the master base position vector $\bar{F}_{MBASE}$ and master base rotation matrix $R_{MBASE}$ values to the values of the currently acquired master position signal $\bar{F}_{MCURR}$ and currently acquired master orientation signal $R_{MCURR}$ respectively.

Referring back to FIG. 3, in addition to storing the current master position and orientation signals $\bar{F}_{MCURR}$ and $R_{MCURR}$ in first and second stores 142 and 144 respectively of the current buffer 140, the master apparatus 64 also stores the calculated values for the position signal $\bar{F}_{EENEW}$ and orientation signal $R_{EENEW}$ of the end effector in the fifth and sixth stores 152 and 154 respectively of the current buffer 140. The base setting block 216 also directs the master apparatus 64 to further store values $x_{sb}$, $y_{sb}$, $z_{sb}$ representing a definable end effector base position vector $\bar{F}_{EEBASE}$ in a seventh store 162 and stores values representing a definable end effector base rotation matrix $R_{EEBASE}$ in a eighth store 164 in the current buffer 140. The end effector base position is shown as a reference frame represented by the axes $x_{sb}$, $y_{sb}$, $z_{sb}$ in FIG. 4. The input device 60 and the master base reference frame represented by the axes $x_{mb}$, $y_{mb}$ and $z_{mb}$ is also shown in FIG. 4. The master apparatus 64 initially causes the definable end effector base position vector $\bar{F}_{EEBASE}$ to be set equal to the new end effector position vector $\bar{F}_{EENEW}$ on startup of the system and causes the definable slave base rotation matrix $R_{EEBASE}$ to define an orientation that is the same as the orientation defined by the new end effector rotation matrix $R_{EENEW}$, on startup of the system. On initialization of the system when there are no previously stored values for $\bar{F}_{EENEW}$ or $R_{EENEW}$, $\bar{F}_{EEBASE}$ and $R_{EEBASE}$ will be set equal to the $\bar{F}_{EENEW}$ and $R_{EENEW}$ defined based on a home configuration of the tool positioning device 81, tool 66 and end effector 73. In this embodiment, the home configuration defines configuration variables to produce a generally straight tool positioning device pose (as shown in FIG. 4) and is preconfigured before initialization of the system. In other embodiments, the home configuration can define configuration variables to produce different bent or both straight and bent tool positioning device poses. Initially, therefore:

$$\bar{F}_{EEBASE} = \bar{F}_{EENEW}; \text{ and}$$

$$R_{EEBASE} = R_{EENEW}$$

In other words, a definable slave base reference frame represented by the axes $x_{sb}$, $y_{sb}$ and $z_{sb}$ and the end effector reference frame represented by the axes $x_5$, $y_5$ and $z_5$ coincide at startup.

The end effector base position vector $\bar{F}_{EEBASE}$ and end effector base rotation matrix $R_{EEBASE}$ are maintained at the same values as on startup until the enablement signal is activated by the footswitch 170 (shown in FIG. 1), which causes the enablement signal to transition from the inactive state to the active state. In response, the base setting block 216 in FIGS. 6 and 7 changes the end effector base position vector $\bar{F}_{EEBASE}$ and end effector rotation matrix $R_{EEBASE}$ to the newly calculated end effector position vector $\bar{F}_{EENEW}$ and newly calculated end effector orientation matrix $R_{EENEW}$.

End Effector Position and Orientation Calculation Block

Figure 8:
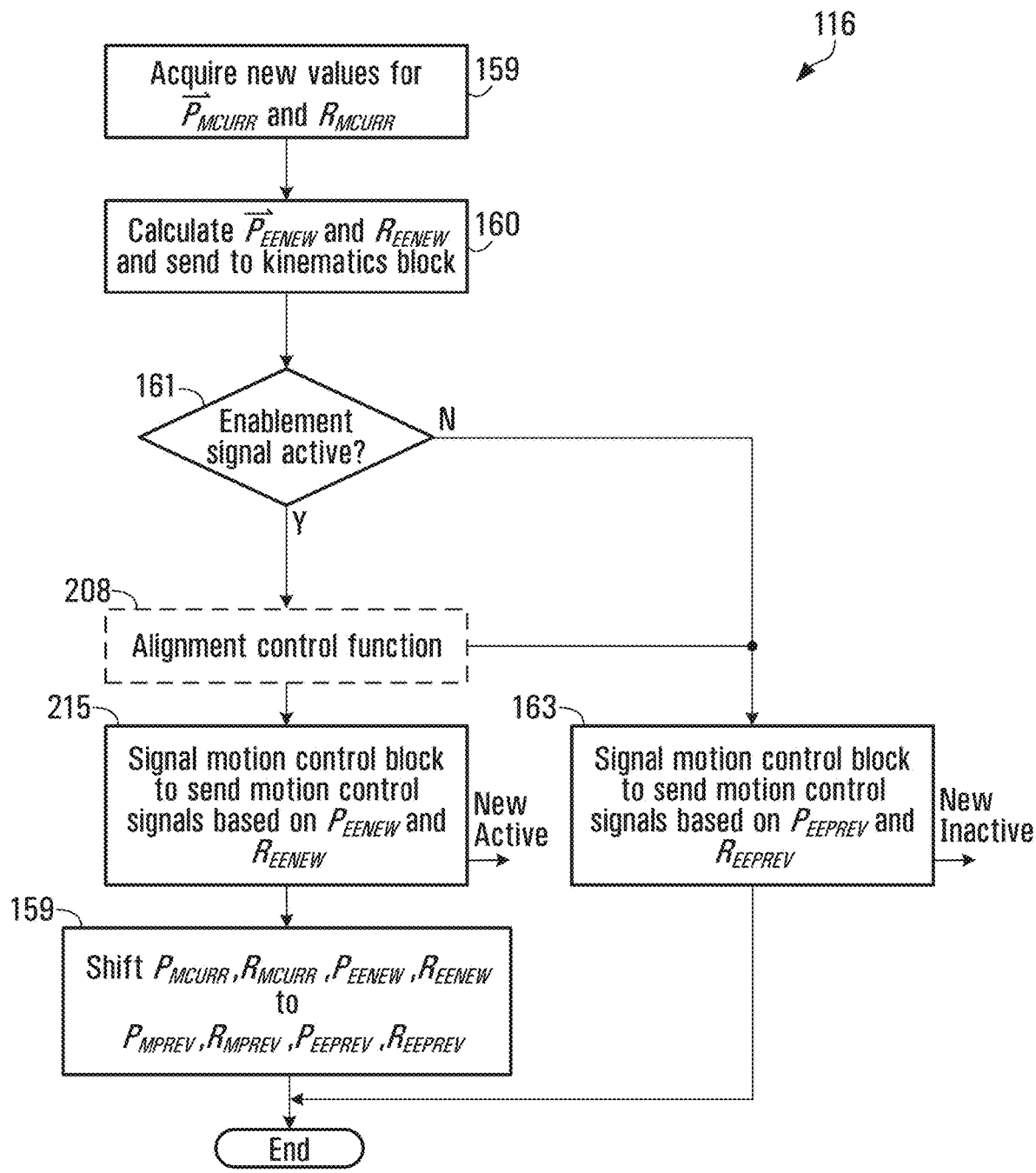
FIG. 8 is a flow chart of an end effector position and orientation calculation block of the flow chart shown in FIG. 6.

Generally, the end effector position and orientation calculation block 116 includes codes that direct the master apparatus 64 to calculate new end effector position and orientation signals, referred to herein as $\bar{F}_{EENEW}$ and $R_{EENEW}$, which position and orient the end effectors 73 into a desired position and orientation in response to the current handle position $\bar{F}_{MCURR}$ and current handle orientation $R_{MCURR}$. In one embodiment the end effector position and orientation calculation block 116 is executed periodically at a rate of about 1 kHz. A flow chart showing details of operations included in the end effector position and orientation calculation block 116 is shown in FIG. 8. The operations begin with block 159 directing the master apparatus 64 to query the control unit 92 of the input device 60 for the current handle position vector $\bar{F}_{MCURR}$ and current handle rotation matrix $R_{MCURR}$. As previously described and referring to FIG. 3, $\bar{F}_{MCURR}$ and $R_{MCURR}$ values are stored by the master apparatus 64, the first store 142 storing the three values representing the current handle position vector $\bar{F}_{MCURR}$ and the second store 144 storing the nine values representing the current handle rotation matrix $R_{MCURR}$.

After new values for $\bar{F}_{MCURR}$ and $R_{MCURR}$ are acquired from the control unit 92, block 160 directs the master apparatus 64 to calculate new end effector position signals $\bar{F}_{EENEW}$ and new end effector orientation signals $R_{EENEW}$ representing a desired end effector position 150 and desired end effector orientation, relative to the fixed slave reference position 128 and the slave base orientation. Block 160 also directs the master apparatus 64 to store, in the fifth store 152 in FIG. 3, values representing the new end effector position vector $\bar{F}_{EENEW}$ and to store, in the sixth store 154 in FIG. 3, values representing the desired end effector orientation matrix $R_{EENEW}$.

The new end effector position signals $\bar{F}_{EENEW}$ and new end effector orientation signals $R_{EENEW}$ are calculated according to the following relations:

$$\bar{F}_{EENEW} = A(\bar{F}_{MCURR} - \bar{F}_{MBASE}) + \bar{F}_{EEBASE} \tag{1a}$$

and $$R_{EENEW} = R_{EEBASE} R_{MBASE}^{-1} R_{MCURR} \tag{1b},$$

where: $\bar{F}_{EENEW}$ is the new end effector position vector that represents the new desired position of the end effector 73 in the end effector workspace, and is defined relative to the slave base reference position;

A is a scalar value representing a scaling factor in translational motion between the master and the slave;

$\bar{F}_{MCURR}$ is the current representation of the handle position vector stored in the first store 142, the handle position vector being defined relative to the fixed master reference frame;

$\bar{F}_{MBASE}$ is the last-saved position vector $\bar{F}_{MCURR}$ for handle 102 that was shifted upon the last inactive to active state transition of the enablement signal such as by release of the footswitch 170 or on system initialization or by operation of a control interface by an operator;

$\bar{F}_{EEBASE}$ is the last saved position vector $\bar{F}_{EENEW}$ for the end effector 73 that was shifted upon the last inactive to active state transition of the enablement signal or on system initialization;

$R_{EENEW}$ is the new end effector orientation matrix representing the current orientation of the end effector 73, and is defined relative to the fixed slave reference position 128;

$R_{EEBASE}$ is the last-saved rotation matrix $R_{EENEW}$ of the end effector 73 shifted upon the last inactive to active state transition of the enablement signal;

$R_{MBASE}^{-1}$ is the inverse of rotation matrix $R_{MBASE}$, where $R_{MBASE}$ is the last-saved rotation matrix $R_{MCURR}$ of the handle 102 saved upon the last inactive to active state transition of the enablement signal;

$R_{MCURR}$ is the currently acquired rotation matrix representing the orientation of the handle 102 relative to the fixed master reference frame;

Block 161 then directs the master apparatus 64 to determine whether or not the enablement signal is in the active state. If the enablement signal is in the active state, optional block 208 directs the master apparatus 64 to execute certain special functions, such as alignment control functions, for example. Such alignment control functions are described in applicant's U.S. applications 62/101,734 and U.S. 62/101, 804, for example, hereby incorporated by reference in their entirety.

Where the special functions are alignment control functions, such functions may have one of two outcomes, for example. The first outcome may direct the master apparatus 64 to execute block 215 which causes the master apparatus 64 to send a "new" signal to the motion control block 120 to signal the motion control block 120 to send slave control signals to the slave computer 74 based on the newly calculated end effector position and newly calculated end effector orientation $\vec{F}_{EENEW}$ and $R_{EENEW}$. The second outcome directs the master apparatus 64 to execute block 163, which causes the master apparatus 64 to set the "new" signal inactive to signal the motion control block 120 to send slave control signals based on a previously calculated end effector position and previously calculated end effector orientation $\vec{F}_{EEPREV}$ and $R_{EEPREV}$.

If block 215 is executed, the slave control signals are based on the newly calculated values for $\vec{F}_{EENEW}$ and $R_{EENEW}$. This causes the end effector 73 to assume a position and orientation determined by the current position and current orientation of the handle 102.

Block 159 then directs the master apparatus 64 to copy the current position vector $\vec{F}_{MCURR}$ and the current rotation matrix $R_{MCURR}$ stored in stores 142 and 144 into stores 143 and 145 of a "previous" buffer 141 referred to in FIG. 3 and to copy newly calculated end effector position vector $\vec{F}_{EENEW}$ and newly calculated end effector rotation matrix $R_{EENEW}$ into stores 147 and 149 of the previous buffer 141. The newly calculated end effector position vector $\vec{F}_{EENEW}$ and newly calculated end effector rotation matrix $R_{EENEW}$ are thus renamed as "previously calculated end effector position vector" $\vec{F}_{EEPREV}$ and "previously calculated end effector rotation matrix" $R_{EEPREV}$. By storing the newly calculated end effector position vector $\vec{F}_{EENEW}$ and newly calculated end effector rotation matrix $R_{EENEW}$, as previously calculated end effector position vector $\vec{F}_{EEPREV}$ and previously calculated end effector rotation matrix $R_{EEPREV}$, a subsequently acquired new end effector position vector $\vec{F}_{EENEW}$ and subsequently acquired new end effector rotation matrix $R_{EENEW}$ can be calculated from the next current handle position vector $\vec{F}_{MCURR}$ and next current handle rotation matrix $R_{MCURR}$.

If block 163 is executed, the slave control signals are based on $\vec{F}_{EEPREV}$ and $R_{EEPREV}$. This causes the end effector 73 to assume a position and orientation determined by a previous position and previous orientation of the handle 102. The end effector position and orientation calculation block 116 is then ended.

Still referring to FIG. 8, at block 161, if the enablement signal is in the inactive state, and while it remains in the inactive state, the master apparatus 64 will immediately execute block 163 which directs the master apparatus 64 to set the "new" signal inactive to indicate to the motion control block 120 in FIG. 5 that it should send the slave control signals based on the previously calculated values of $\vec{F}_{EEPREV}$ and $R_{EEPREV}$ in stores 147 and 149, respectively. The slave control signals produced by the motion control block 120 thus represent control wire length values derived from the last saved values of $\vec{F}_{EENEW}$ and $R_{EENEW}$, causing the end effector 73 to remain stationary because the same slave control signals as were previously determined are sent to the slave computer 74. The end effector position and orientation calculation block 116 is then ended. As long as the enablement signal is inactive, slave control signals are based only on the previously calculated end effector position and previously calculated orientation signals $\vec{F}_{EEPREV}$ and $R_{EEPREV}$ as they exist before the enablement signal became inactive.

Accordingly, when the enablement signal is in the inactive state, the handle 102 can be moved and rotated and the calculations of $\vec{F}_{EENEW}$ and $R_{EENEW}$ will still be performed by block 160 of the end effector position and orientation calculator block 116, but there will be no movement of the end effector 73, because the previous slave control signals are sent to the slave computer 74. This allows "clutching" or repositioning the handle 102 without corresponding movement of the end effector 73 and enables the end effector 73 to have increased range of movement and allows the operator to reposition their hands to a comfortable position within the handle translational workspace.

While it has been shown that either the previously calculated end effector position and previously calculated orientation signals $\vec{F}_{EENEW}$ and $R_{EEPREV}$ or the newly calculated end effector position and newly calculated orientation $\vec{F}_{EENEW}$ and $R_{EENEW}$ are used as the basis for producing the slave control signals sent by the motion control block 120 to the slave computer 74, the newly calculated end effector position and newly calculated end effector orientation signals $\vec{F}_{EENEW}$ and $R_{EENEW}$ are always presented to the kinematics block 118 and the feedback force control block 122. In other words, the kinematic block 118 always calculates the configuration variables based on the newly calculated end effector position and newly calculated end effector orientation signals $\vec{F}_{EENEW}$ and $R_{EENEW}$, and the feedback force control block 122 always calculates the theoretical locations of various points along the tool positioning device and the distance between the various points on the left tool positioning device and the various points on the right tool positioning device based on $\vec{F}_{EENEW}$ and $R_{EENEW}$.

Kinematics Block

The kinematics block 118 includes codes that direct the master apparatus 64 to produce configuration variables in response to the newly calculated end effector position and orientation signals $\vec{F}_{EENEW}$ and $R_{EENEW}$. The configuration variables define a tool positioning device pose required to position and orient the end effector 73 into the desired end effector position and orientation.

The kinematics block 118 receives newly calculated end effector position and orientation signals $\vec{F}_{EENEW}$ and $R_{EENEW}$ each time the end effector position and orientation calculation block 116 is executed. In response, the kinematics block 118 produces configuration variables for the tool positioning device 81.

Figure 9:
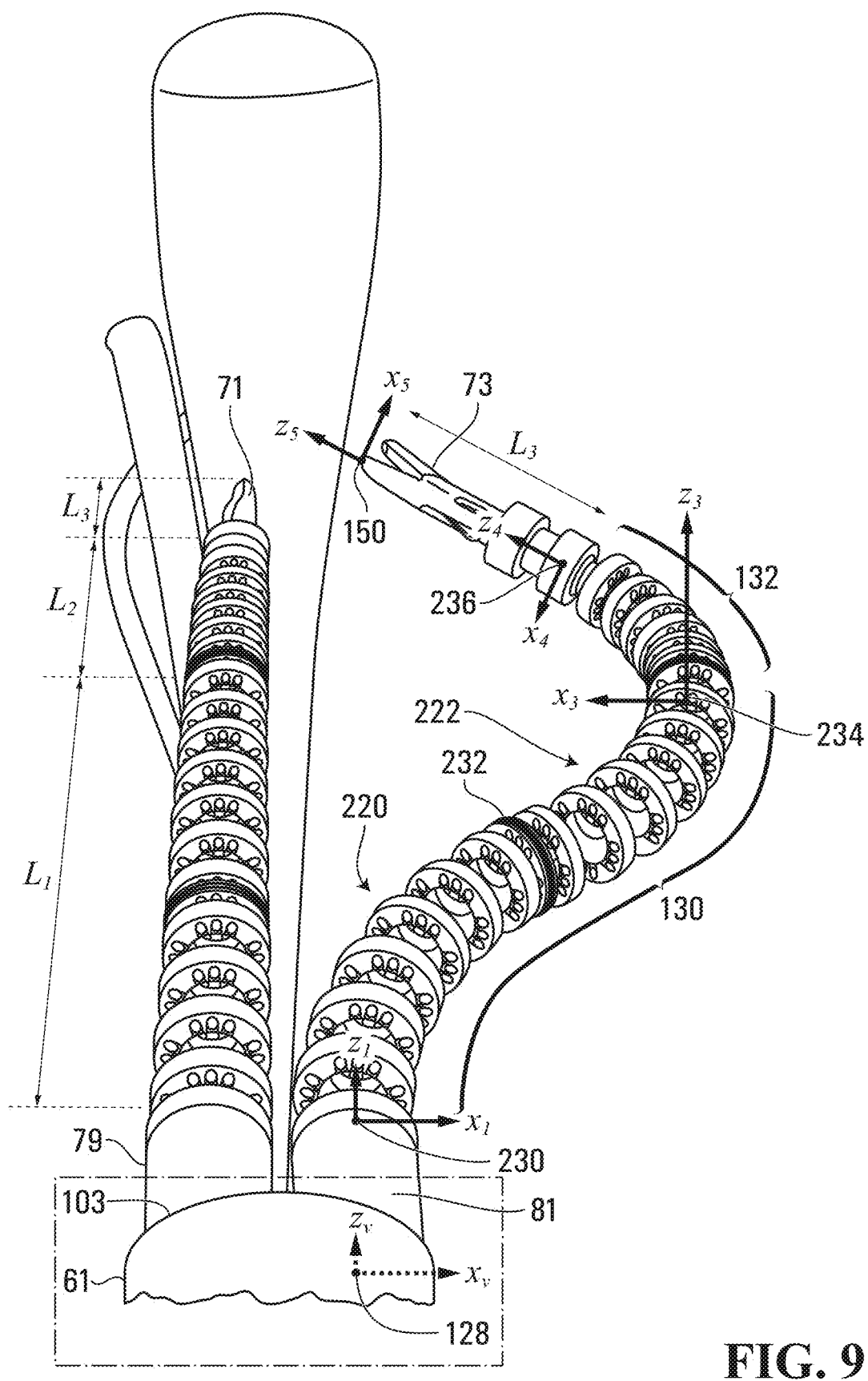
FIG. 9 is a perspective view of left and right hand tool positioning devices of the slave subsystem shown in FIG. 1.

Referring to FIGS. 5 and 9, the tool positioning device 81 has a first articulated segment 130, referred to as an s-segment and a second articulated segment 132 referred to as a distal segment. The segments each include a plurality of "vertebra" 224. The s-segment 130 begins at a distance from the insertion tube 61, referred to as the insertion distance $q_{ins}$, which is the distance between the fixed slave reference position 128 defined as the origin of the slave fixed base reference frame $x_v, y_v, z_v$ and a first position 230 at the origin of a first position reference frame $x_1$, $y_1$, and $z_1$ (shown in FIG. 9). The insertion distance $q_{ins}$ represents an unbendable portion of the tool positioning device 81 that extends out of the end of the insertion tube 61. In the embodiment shown, the insertion distance $q_{ins}$ may be about 10-20 mm, for example. In other embodiments, the insertion distance $q_{ins}$ may be longer or shorter, varying from 0-100 mm, for example.

The s-segment 130 extends from the first position 230 to a third position 234 defined as an origin of a third reference frame having axes $x_3$, $y_3$, and $z_3$ and is capable of assuming a smooth S-shape when control wires (not shown) inside the s-segment 130 are pushed and pulled. The s-segment 130 has a mid-point at a second position 232, defined as the origin of a second position reference frame having axes $x_2$, $y_2$, $z_2$. The s-segment 130 has a length $L_1$, seen best on the left-hand side tool positioning device 79 in FIG. 9. In the embodiment shown, this length $L_1$ may be about 65 mm, for example.

The distal segment 132 extends from the third position 234 to a fourth position 236 defined as an origin of a fourth reference frame having axes $x_4$, $y_4$, $z_4$. The distal segment 132 has a length $L_2$ also seen best on the left-hand side tool positioning device 79 in FIG. 9. In the embodiment shown, this length $L_2$ may be about 23 mm, for example.

Each tool 66 and 67 also has an end effector length, which in the embodiment shown is a gripper length $L_3$ that extends from the fourth position 236 to the end effector position 150 defined as the origin of axes $x_5$, $y_5$, and $z_5$. The gripper length $L_3$ is again best seen on the left-hand side tool positioning device 79 in FIG. 9 and in this embodiment may be about 25 mm, for example. The slave reference position 128, first position 230, second position 232, third position 234, fourth position 236 and end effector position 150 may collectively be referred to as tool reference positions.

As explained in PCT/CA2013/001076, hereby incorporated herein by reference in its entirety, by pushing and pulling on certain control wires inside the tool positioning devices 79 and 81, the s-segment 130 can be bent into any of various degrees of an S-shape, from straight as shown in FIG. 9 on the left hand tool positioning device 81 to a partial S-shape as shown in FIG. 9 on the right hand tool positioning device 79 to a full S-shape. The s-segment 130 is sectional in that it has a first section 220 and a second section 222 on opposite sides of the second position 232. Referring now to FIG. 5, the first and second sections 220 and 222 lie in a first bend plane containing the first position 230, second position 232, and third position 234. The first bend plane is at an angle $\delta_{prox}$ to the $x_v$-$z_v$ plane of the fixed slave reference frame. The first section 220 and second section 222 are bent in the first bend plane through opposite but equal angles $\theta_{prox}$ such that no matter the angle $\theta_{prox}$ or the bend plane angle $\delta_{prox}$, the $z_3$ axis of the third position 234 is always parallel to and aligned in the same direction as the $z_v$ axis of the fixed slave reference position 128. Thus, by pushing and pulling on the control wires within the tool positioning device 81, the third position 234 can be placed at any of a number of discrete positions within a cylindrical volume in space. This volume may be referred to as the s-segment workspace.

In addition, the distal segment 132 lies in a second bend plane containing the third position 234 and the fourth position 236. The second bend plane is at an angle $\delta_{dist}$ to the $x_v$-$z_v$ plane of the fixed slave reference frame. The distal segment 132 is bent in the second bend plane at an angle $\theta_{dist}$. Thus, by pushing and pulling the control wires within the tool positioning device 81, the fourth position 236 can be placed within another volume in space. This volume may be referred to as the distal workspace. The combination of the s-segment workspace plus the distal workspace can be referred to as the tool positioning device workspace, as this represents the total possible movement of the tools 66 and 67 as effected by the respective tool positioning devices 79 and 81.

The distance between the fourth position 236 and the end effector position 150 is the distance between the movable portion of the distal segment 132 and the tip of the gripper end effector 73 (and 73) in the embodiment shown, i.e. the length the gripper length $L_3$. Generally, the portion of the gripper between the fourth position 236 and the end effector position 150 ($L_3$) will be unbendable.

In the embodiment shown, the end effector 71 or 73 is a gripper jaw tool that is rotatable about the $z_5$ axis in the $x_5$-$y_5$ plane of the end effector reference frame, the angle of rotation being represented by an angle γ relative to the positive $x_5$ axis. Finally, the gripper jaws may be at any of varying degrees of openness from fully closed to fully open (as limited by the hinge). The varying degrees of openness may be defined as the "gripper".

In summary therefore, the configuration variables provided by the kinematic block 118 codes are:

$q_{ins}$: represents a distance from the slave reference position 128 defined by axes $x_v$, $y_v$, and $z_v$ to the first position 230 defined by axes $x_1$, $y_1$ and $z_1$ where the s-segment 130 of the tool positioning device 81 begins;

$\delta_{prox}$: represents a first bend plane in which the s-segment 130 is bent relative to the $x_v$-$y_v$ plane of the fixed slave reference frame;

$\theta_{prox}$: represents an angle at which the first and second sections 220 and 222 of the s-segment 130 is bent in the first bend plane;

$\delta_{dist}$: represents a second bend plane in which the distal segment 132 is bent relative to the $x_v$-$y_v$ plane of the fixed slave reference frame;

$\theta_{dist}$: represents an angle through which the distal segment 132 is bent in the second bend;

γ: represents a rotation of the end effector 73 about axis $z_5$; and

Gripper: represents a degree of openness of the gripper jaws of the end effector 73. (This is a value which is calculated in direct proportion to a signal produced by an actuator (not shown) on the handle 102 indicative of an amount of pressure the operator exerts by squeezing the handle).

To calculate the configuration variables, it will first be recalled that the end effector rotation matrix $R_{EENEW}$ is a 3×3 matrix:

$$\begin{bmatrix} x_{5x} & y_{5x} & z_{5x} \\ x_{5y} & y_{5y} & z_{5y} \\ x_{5z} & y_{5z} & z_{5z} \end{bmatrix}.$$

Since the last column of $R_{EENEW}$ is the z-axis of the end effector reference frame written relative to the fixed slave reference frame $y_v$, $y_v$ and $z_v$, the values $\theta_{dist}$, $\delta_{dist}$, and $\gamma$ associated with the distal segment 132 can be calculated according to the relations:

$$\theta_{dist} = \frac{\pi}{2} - a\tan2\left(\sqrt{z_{5x}^2 + z_{5y}^2}, z_{5z}\right) \tag{2}$$

$$\delta_{dist} = -a\tan2(z_{5y}, z_{5x}) \tag{3}$$

If $|\delta_2| > \frac{n}{2} |\delta_{dist}| > \frac{\pi}{2}$ $$\gamma = a\tan2(-y_{5z}, x_{5z}) - \delta_{dist} + \pi \tag{4a}$$

else $$\gamma = a\tan2(y_{5z}, -x_{5z}) - \delta_{dist} \tag{4b}$$
$$\gamma = a\tan2(R_{ee_{3,2'}} - R_{ee_{3,1}}) - \delta_2$$

These values can then be used to compute the location of third position 234 ($\bar{p}_{3/v}$) relative to the fixed slave reference position 128 by computing the vectors from the third position 234 to the fourth position 236 ($\bar{p}_{4/3}$) and from the fourth position 236 to the end effector position 150 ($\bar{p}_{5/4}$) and subtracting those vectors from $\bar{F}_{EENEW}$.

$$\bar{p}_{3/s} = \bar{p}_{EENEW} - \bar{p}_{4/3} - \bar{p}_{5/4}, \tag{5}$$

where:

$$\bar{p}_{4/3} \cdot \bar{i} = \frac{-L_2 \cos\delta_{dist}(\sin\theta_{dist} - 1)}{\frac{\pi}{2} - \theta_{dist}} \bar{p}_{4/3} \cdot \bar{i} = \frac{-L_2 \cos\delta_2(\sin(\theta_2) - 1)}{\frac{\pi}{2} - \theta_2} \tag{6a}$$

$$\bar{p}_{4/3} \cdot \bar{j} = \frac{L_2 \sin\delta_{dist}(\sin\theta_{dist} - 1)}{\frac{\pi}{2} - \theta_{dist}} \tag{6b}$$

$$\bar{p}_{4/3} \cdot \bar{k} = \frac{L_2 \cos(\theta_{dist})}{\frac{\pi}{2} - \theta_{dist}} \tag{6c}$$

$$\bar{p}_{5/4} \cdot \bar{i} = L_3 \cos(\delta_{dist}) \cos(\theta_{dist}) \tag{7a}$$

$$\bar{p}_{5/4} \cdot \bar{j} = -L_3 \sin(\delta_{dist}) \cos(\theta_{dist}) \tag{7b}$$

$$\bar{p}_{5/4} \cdot \bar{k} = L_3 \sin(\theta_{dist}), \tag{7c}$$

and where:

$\bar{i}$ is a unit vector in the x direction;
$\bar{j}$ is a unit vector in the y direction; and
$\bar{k}$ is a unit vector in the z direction.

Once the vector from the fixed slave reference position 128 to the third position 234 ($\bar{F}_{3/v}$) is known, the configuration variables, $\delta_{prox}$ and $\theta_{prox}$, for the s-segment 130 can be found. $\delta_{prox}$ associated with the s-segment 130 is calculated by solving the following two equations for $\delta_{prox}$:

$$\bar{p}_{3/v} \cdot \bar{i} = \frac{-L_1 \cos\delta_{prox}(\sin\theta_{prox} - 1)}{\frac{\pi}{2} - \theta_{prox}} \tag{8a}$$

$$\bar{p}_{3/v} \cdot \bar{j} = \frac{L_1 \sin\delta_{prox}(\sin\theta_{prox} - 1)}{\frac{\pi}{2} - \theta_{prox}}. \tag{8b}$$

The ratio of (8b) and (8a) gives $$\delta_{prox} = a\tan 2(-\bar{p}_{3/v} \cdot \bar{j}, \bar{p}_{3/v} \cdot \bar{i}), \tag{9}$$

where $\bar{i}$ and $\bar{j}$ are unit vectors in the x and y directions respectively.

A closed form solution cannot be found for $\theta_{prox}$, thus $\theta_{prox}$ must be found with a numerical equation solution to either of equations (8a) or (8b). A Newton-Raphson method, being a method for iteratively approximating successively better roots of a real-valued function, may be employed, for example. The Newton-Raphson method can be implemented using the following equations:

$$f(\theta_{prox}) = \frac{L_1}{\frac{\pi}{2} - \theta_{prox}} \cos\delta_{prox}(1 - \sin\theta_{prox}) - \bar{p}_{3/v} \cdot \bar{i} = 0, \tag{10}$$

where
$\bar{i}$ is the unit vector in the x direction; and
$\bar{p}_{3/v}$ is a vector from the fixed slave reference position 128 to the third position 234.

The equation (10) is equation (8a) rewritten in the form $f(\theta_{prox}) = -0$. The Newton-Raphson method tends to converge very quickly because in the range $0<\theta_{prox}<\pi$, the function has a large radius of curvature and has no local stationary points. Following the Newton-Raphson method, successive improved estimates of $\theta_{prox}$ can be made iteratively to satisfy equation (10) using the following relationship:

$$\theta_{n+1} = \theta_n - \frac{f(\theta_n)}{f'(\theta_n)} \tag{11}$$

Finally, upon determination of $\theta_{prox}$, the following equation can be used to find $q_{ins}$, $$q_{ins} = -\bar{p}_{3/v} \cdot \bar{k} - \frac{L_1 \cos\theta_{prox}}{\frac{\pi}{2} - \theta_{prox}}, \tag{12}$$

where:
$\bar{k}$ is the unit vector n the z direction;
$\bar{p}_{3/v}$ is a vector from the fixed slave reference position 128 to the third position 234; and
$\bar{p}_{3/v} \cdot \bar{k}$ is the dot product of the vector $\bar{p}_{3/v}$ and the unit vector $\bar{k}$.

The codes in the kinematics block 118 shown in FIG. 6 direct the master apparatus 64 to calculate values for the above configuration variables in response to the end effector position and orientation signals $\bar{F}_{EENEW}$ and $R_{EENEW}$ produced by the end effector position and orientation calculation block 116 and these calculated configuration variables generally define a tool positioning device pose required to position the end effector 71 or 73 at a desired location and at a desired orientation in the end effector workspace.

It will be appreciated that configuration variables are produced for each end effector 71 and 73 and therefore in the embodiment shown, two sets of configuration variables which will be referred to as left and right configuration variables respectively are produced and forwarded or otherwise made available to the motion control block 120 and feedback force control block 122.

Feedback Force Control Block

Referring back to FIG. 6, the feedback force control block 122 directs the master apparatus 64 to receive the left and right configuration variables from the kinematics blocks 118 executed for both the left and right end effectors 71 and 73 respectively and to determine a theoretical location in the tool positioning device workspace of various points along each of the tool positioning devices 79 and 81. The feedback force control block 122 also directs the master apparatus 64 to determine whether a distance between any two theoretical locations located on separate tool positioning devices is less than a threshold distance. When such distance is less than the threshold distance, the codes of the feedback force control block 122 direct the master apparatus 64 to cause the operator to be notified of the proximity. Notifying the operator of this proximity may be provided by visual means through the LCD display 68 in the viewer 62 and/or by audio means and/or by providing haptic feedback using the input devices 58 and 60, for example.

Figure 10:
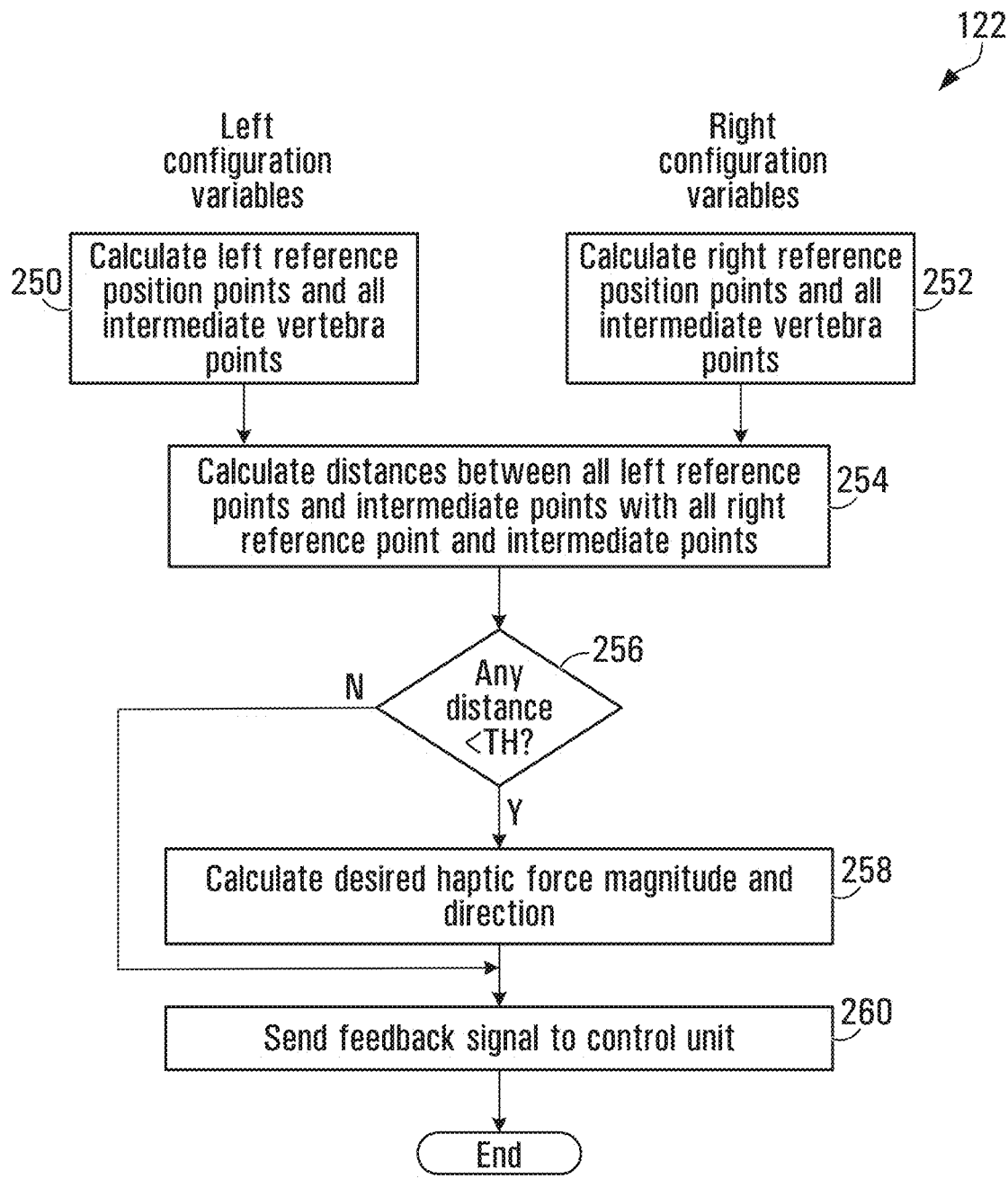
FIG. 10 is a flowchart representing codes executed by a master apparatus of the master subsystem shown in FIG. 1, to provide for computation of proximity laparoscopic surgical tools.

A flow chart showing details of operations included in the feedback force control block 122 is shown in FIG. 10. Referring to FIG. 10, the feedback force control block 122 includes blocks 250 and 252 that respectively receive the left and right configuration variables produced by the kinematics block 118. Blocks 250 and 252 direct the master apparatus 64 to use the methods described below to perform the calculations required to determine, relative to the fixed slave reference position 128 and thus in absolute terms within the tool positioning device workspace and end effector workspace, the theoretical locations of each of the tool reference points, namely a first position 230, a second position 232, a third position 234, a fourth position 236 and the end effector position 150, for both the left and right hand tool positioning devices 79 and 81 and end effectors 71 and 73.

Once the theoretical location of each reference point is determined, the theoretical locations of various intermediate points along the tool positioning devices 79 and 81 within the tool positioning device workspace may then be determined. Each of the sections 220, 222 of the s-segment 130 and the distal segment 132 of the tool positioning devices 79 and 81 is comprised of a plurality of the identical "vertebra" 224 generally extending between first position 230 and fourth position 236 and the centers of the vertebrae are spaced apart by the same distance, and the intermediate points are defined as a position at the center of each identical vertebra of respective tool positioning devices 79 and 81. Since the s-segment 130 and distal segments 132 form smooth continuous constant-radius curves when bent, the theoretical location of the center of each vertebra can be calculated mathematically.

For example, for any given tool positioning device 79 or 81, the theoretical location of the first position 230 reference point relative to the fixed slave reference position 128 can be determined through simple addition of the $q_{ins}$ configuration variable determined by the kinematics block 118 to the fixed slave reference position 128 in the $z_v$ axis, as the $q_{ins}$ generally represents an unbendable portion of the tool positioning device. Determining the vector from the fixed slave reference position 128 to the first position 230 ($\vec{F}_{1/v}$) will provide a theoretical location of the first position 230 in absolute terms within the tool positioning device workspace.

Once the theoretical location of the first position 230 is determined, the theoretical location of all vertebrae 224 in the first section 220 of the s-segment 130, namely from the first position 230 to the second position 232, can be determined. For example in the embodiment shown in FIG. 9, assuming there are 15 vertebrae 224 in the first section 220, extending from the first position 230 to the second position 232. The center of the $n^{th}$ vertebrae of the first section 220 would lie at a theoretical location that is at an intermediate point along the first section 220, and the intermediate point can be calculated as $$n * \frac{1}{15} * \theta_{prox}$$

relative to the first position 230 reference point. A vector from the first position 230 to the $n^{th}$ vertebra position can then be determined. Adding the vector from the first position 230 to the $n^{th}$ vertebrae to the vector from the fixed slave reference position 128 to the first position 230 ($\vec{F}_{1/v}$) will arrive at the theoretical location of the vertebrae of the first section 220 in absolute terms in the positioning device workspace, relative to the fixed slave reference position 128. This procedure is done for each of the 15 vertebrae in the first section 220 of the s-segment 130 to find the theoretical location relative to the fixed slave reference position 128 for each of the vertebra 224 of the first section 220 within the tool positioning device workspace.

Additionally, for any given tool positioning device 79 or 81, the theoretical location of the second position 232 reference point relative to the fixed slave reference position 128 can be determined from the configuration variables $q_{ins}$, $\theta_{prox}$ and $\delta_{prox}$. Determining a vector from the fixed slave reference position 128 to the second position 232 ($\vec{F}_{2/v}$) will provide a theoretical location of the second position 232 in absolute terms within the tool positioning device workspace.

Once the theoretical location of the second position 232 is determined, it is used as the reference point for the determination of the theoretical location of all vertebrae intermediate points in the second section 222 of the s-segment 130, namely extending from the second position 232 to the third position 234. For the embodiment of the tool positioning device 81 shown in FIG. 9, assuming again that there are 15 vertebrae in the second section 222, the center of the $n^{th}$ vertebrae of the second section 222 would lie in an intermediate point along the second section 222. The angle the second section 222 is bent in the first bend plane $\delta_{prox}$ is equal and opposite to the angle $\theta_m$ used for the calculations concerning the vertebrae of the first section 220. Therefore, intermediate point of the $n^{th}$ vertebrae can be calculated as $$n * \frac{1}{15} * -\theta_{prox}$$

relative to the second position 232. Adding the vector from the second position 232 reference point to the $n^{th}$ vertebra to the vector from the slave reference position 128 to the second position 232 ($\vec{F}_{2/v}$) will provide the theoretical location of the $n^{th}$ vertebrae of the second section 222 in absolute terms within the tool positioning device workspace. This procedure is done for each of the 15 vertebrae in the second section 220 of the s-segment 130 to find the absolute positions for each vertebrae intermediate point within the tool positioning device workspace, relative to the fixed slave reference position.

Additionally, for any given tool positioning device 79 or 81, the theoretical location of the third position 234, which is at the end of the s-segment 130, can be expressed by a vector $\vec{F}_{3/v}$ defined by the following vector components expressed relative to the fixed slave reference position:

$$\overline{p}_{3/v} \cdot \vec{i} = \frac{-L_1 \cos\delta_{prox}(\sin\theta_{prox} - 1)}{\frac{\pi}{2} - \theta_{prox}} \quad (8a)$$

$$\overline{p}_{3/v} \cdot \vec{j} = \frac{L_1 \sin\delta_{prox}(\sin\theta_{prox} - 1)}{\frac{\pi}{2} - \theta_{prox}} \quad (8b)$$

$$\overline{p}_{3/v} \cdot \vec{k} = q_{ins} + \frac{L_1 \cos\theta_{prox}}{\frac{\pi}{2} - \theta_{prox}} \quad (8c)$$

Once the theoretical location of the third position 234 is determined, it can be used as the reference point to determine the theoretical location of all vertebrae 224 in the distal segment 132 using the method provided above. Assuming that there are 15 vertebrae in the distal segment 132, the center of the $n^{th}$ vertebrae would lie in an intermediate point that is along the distal segment 132. The angle the distal segment 132 is bent in the second bend plane $\delta_{dist}$ is $\theta_{dist}$. Therefore, the intermediate point of the $n^{th}$ vertebrae can be calculated as $$n * \frac{1}{15} * \theta_{dist}$$

relative to the third position 234. Adding the vector from the third position 234 reference point to the $n^{th}$ vertebra intermediate point in the distal segment 132 to the vector from the fixed slave reference position 128 to third position 234 ($\overline{F}_{3/v}$) will arrive at the theoretical location of the $n^{th}$ vertebrae in the distal segment 132 in absolute terms in the tool positioning device workspace. This procedure is done for each of the 15 vertebrae in the distal segment 132 to find the theoretical location for each vertebrae intermediate point in the tool positioning device workspace in absolute terms, relative to the fixed slave reference position 128.

Further, the theoretical location of the fourth position 236 reference point can be determined as a vector relative to the third position 234 ($\overline{F}_{4/3}$) according to the following vector component relations, as previously presented:

$$\overline{p}_{4/3} \cdot \vec{i} = \frac{-L_2 \cos\delta_{dist}(\sin\theta_{dist} - 1)}{\frac{\pi}{2} - \theta_{dist}} \overline{p}_{4/3} \cdot \vec{i} = \frac{-L_2 \cos\delta_2(\sin(\theta_2) - 1)}{\frac{\pi}{2} - \theta_2} \quad (6a)$$

$$\overline{p}_{4/3} \cdot \vec{j} = \frac{L_2 \sin\delta_{dist}(\sin\theta_{dist} - 1)}{\frac{\pi}{2} - \theta_{dist}} \quad (6b)$$

$$\overline{p}_{4/3} \cdot \vec{k} = \frac{L_2 \cos(\theta_{dist})}{\frac{\pi}{2} - \theta_{dist}} \quad (6c)$$

Adding the vector from the third position 234 reference point to the fourth position 236 reference point ($\overline{F}_{4/3}$) to the vector from the fixed slave reference position 128 to the third position 234 ($\overline{F}_{3/v}$) will arrive at the theoretical location of the fourth position 236 reference point in absolute terms relative to the fixed slave reference position 128 in the tool positioning device workspace.

Finally, the theoretical location of the end effector position 150 reference point can be determined as a vector relative to the fourth position 236 ($\overline{F}_{5/4}$) according to the following vector component relations, as previously presented:

$$\overline{p}_{5/4} \cdot \vec{i} = L_3 \cos(\delta_{dist})\cos(\theta_{dist}) \quad (7a)$$

$$\overline{p}_{5/4} \cdot \vec{j} = -L_3 \sin(\delta_{dist})\cos(\theta_{dist}) \quad (7b)$$

$$\overline{p}_{5/4} \cdot \vec{k} = L_3 \sin(\theta_{dist}) \quad (7c)$$

Adding the vector from the fourth position 236 reference point to the end effector position 150 reference point ($\overline{p}_{5/4}$) to the vector from the third position 234 reference point to the fourth position 236 reference point ($\overline{p}_{4/3}$) and to the vector from the fixed slave reference position 128 to the third position 234 reference point ($\overline{p}_{3/v}$) will arrive at the theoretical location of the end effector position 150 in absolute terms relative to the fixed slave reference position 128 in the end effector workspace.

Following calculation of the theoretical location of reference position points and intermediate vertebra points of the left and right tool positioning devices 79 and 81 and end effectors 71 and 73 at blocks 250 and 252, block 254 of the feedback force control block 122 directs the master apparatus 64 to calculate the distance between each reference point and intermediate point associated with the left-hand tool positioning device 79 and each reference point and intermediate point associated with the right-hand tool positioning device 81. This is done simply by the following vector calculation:

$$d = |\overline{p}_L - \overline{p}_R|, \quad (14)$$

where:
$\overline{p}_L$ is a vector to the point of interest, defined as either a reference point or an intermediate point, on the left tool positioning device 79 or left end effector 71;
$\overline{p}_R$ is a vector to the point of interest, defined as either a reference point or an intermediate point, on the right tool positioning device 81 or right end effector 73; and
d=calculated distance.

Figure 12:
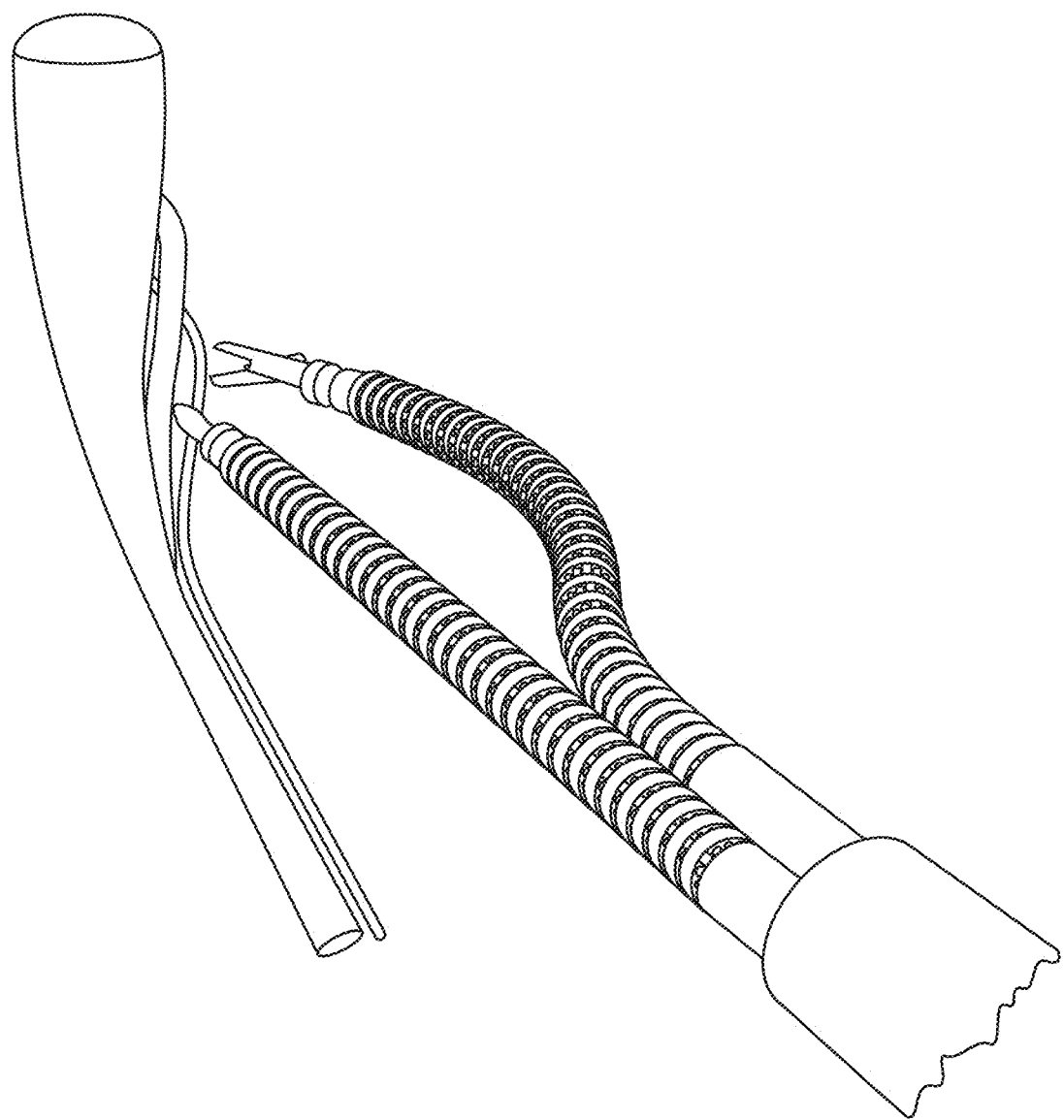
FIG. 12 is a perspective view of left and right hand tool positioning devices of the slave subsystem shown in FIG. 1 where the proximity criterion is not met.
Figure 13:
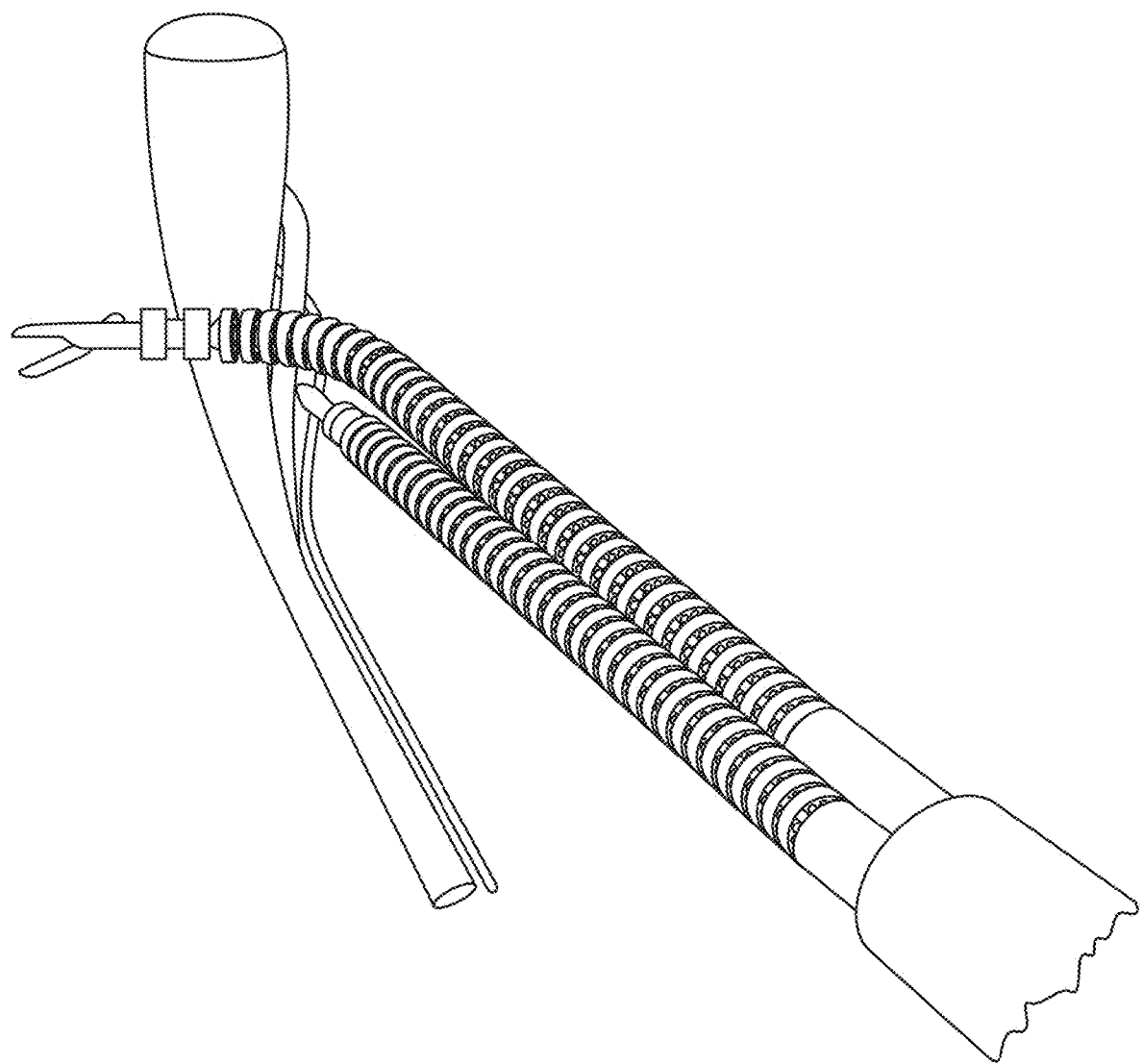
FIG. 13 is a perspective view of left and right hand tool positioning devices of the slave subsystem shown in FIG. 1 where the proximity criterion is met.

Upon calculating the distances between all left points of interest associated with left tool positioning device 79 and all right points of interest associated with the right tool positioning devices 81, block 256 then directs the master apparatus 64 to determine whether any calculated distance between any two points of interest on the separate tool positioning devices 79 and 81 meets a proximity criterion. In this embodiment, the proximity criterion is whether the calculated distance between the two points of interest is less than a threshold distance (TH). Specifically, as illustrated in FIG. 12, the proximity criterion is not met when the calculated distance between the two points of interest is greater or equal to the threshold distance and, as illustrated in FIG. 13, the proximity criterion is met when the calculated distance between the two points of interest is less than the threshold distance. The threshold distance may be set relative to the diameters of the tool positioning devices. In one embodiment the threshold distance may be set to a distance of no less than 1 diameter of the tool positioning devices 79 and 81 since the tool positioning devices physically cannot assume a pose where their axes are spaced closer than 1 diameter. A safe threshold may be about 2 tool holder diameters, for example.

It will be appreciated that the signals representing newly calculated end effector positions $\overline{F}_{EENEW}$ and orientation $R_{EENEW}$ for any two tool positioning devices 79 and 81 may specify end effector positions for each end effector 71 and 73 associated with the tool positioning devices that seek to pose the two tool positioning devices such that two points would physically occupy the same theoretical location in space at the same time ("coincide") or place a point on the right tool positioning device 81 to the left of the left tool positioning device 79 ("cross"). Of course, these are not positions that can actually be attained because, physically, two points cannot occupy the same location in space at the same time nor can one tool positioning device penetrate the solid matter of the second tool positioning device. However, the theoretical locations of points of interest along each tool positioning device calculated by the feedback force control block 122 can define coinciding positions or crossing positions.

In any situation where any theoretical location of one point on the left tool positioning device 79 or end effector 71 is closer to the theoretical location of one point on the right tool positioning device 81 or end effector 73 than the threshold distance and thus meet the proximity criterion, the two points are said to "overlap". There may be different degrees of overlap, calculated from the amount of difference between the calculated distance between the two points and the threshold distance (the "overlap distance"), for example.

If any calculated distance between two points on the tool positioning devices 79 and 81 or end effectors 71 and 73 overlap in the embodiment shown in FIG. 10, block 258 directs the master apparatus 64 to calculate a haptic force magnitude and direction dependent on the degree of overlap. In other embodiments, block 258 may direct the master apparatus 64 to produce a visual or audio annunciation signal.

The magnitude of the haptic force may be determined using a defined function of the overlap distance between the point of interest on the left tool positioning device 79 and end effector 71 and the point of interest on the right tool positioning device 81 and end effector 73. For example, the force magnitude may be proportional to the square of the overlap distance multiplied by a scaling factor. For example, the magnitude of the haptic force may be calculated according to the relation:

$$F = 0.35(\text{overlap distance})^2. \quad (15)$$

The direction of the haptic force may be determined by computing a unit vector normal to a point of contact, where the point of contact is defined as the point midway along the vector between $\bar{p}_R$ and $\bar{p}_L$ when the distance between $\bar{p}_R$ and $\bar{p}_L$ is equal to the threshold distance. For example, the force direction can be computed using vector addition. The force direction on the right tool positioning device 81 and end effector 73 may be computed by subtracting the vector to the point of interest on the left instrument ($\bar{p}_L$) from the vector to the point of interest on the right instrument ($\bar{p}_L$), and then normalizing to give a unit vector $\bar{e}_R$ by the relation:

$$\bar{e}_R = \frac{\bar{p}_R - \bar{p}_L}{|\bar{p}_R - \bar{p}_L|} \quad (16)$$

In one embodiment; the force direction on the left tool positioning device 79 and end effector 71 may be in the opposite direction to the force direction on the right tool positioning device 81 and end effector 73 so that to the operator, the forces presented by input devices 58 and 60 are equal but opposite, thus simulating contact between the tool positioning devices 79 and 81.

Figure 11:
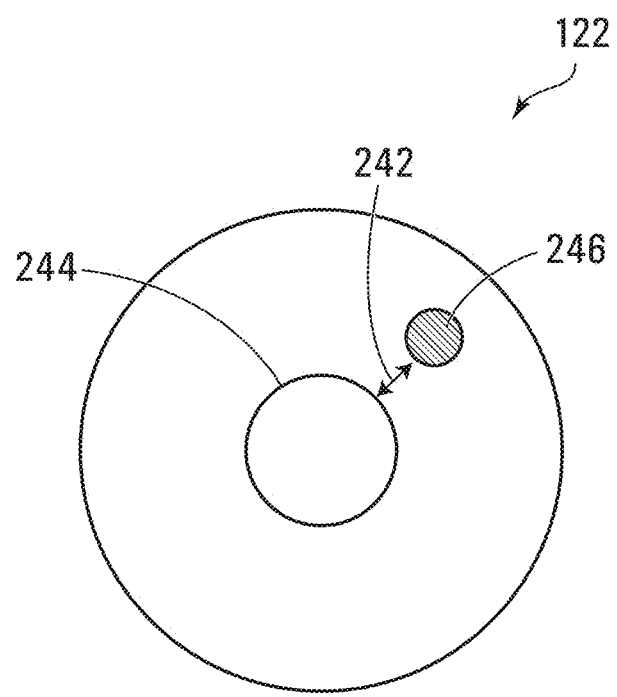
FIG. 11 is a schematic diagram of a visual representation of proximity of the left and right handed tool positioning devices.

Block 260 then directs the master apparatus 64 to produce a feedback signal for receipt by the control unit 92. In this embodiment the feedback signal causes the control unit 92 to produce a haptic force detectable by the operator, to indicate to the operator that the tool positioning devices are in close proximity. For example, the feedback signal may include a representation of the magnitude of haptic force to be felt by the operator in equal and opposite directions normal to the contact tangent plane so as to feel to the operator as though the instruments are touching one another. Alternatively, the feedback signal can be used to produce display control signals for causing the viewer 62 in FIG. 1, for example to show the closest points of approach on the left and right tool positioning devices 79 and 81. For example, referring to FIG. 11, the view can show the left tool positioning device as a first circle 244, the right tool positioning device as a second circle 246 and a line 242 between the first and second circles representing the nearest distance calculated by block 256. After the feedback signal is sent to the control unit at block 260, the feedback force control block 122 is then ended.

If, at block 256, none of the calculated distances between two points are less than the threshold distance, i.e. they are all equal to or more than the threshold distance, then block 260 of feedback force control block 122 directs the master apparatus 64 send a feedback signal that causes the input device to stop causing haptic force to be produced based on collision detection. If no other feedback producing systems are requesting haptic force feedback, the master apparatus 64 produces a feedback signal for receipt by the control unit 92 to cause the control unit to cease producing any haptic force previously detectable by the operator, indicating to the operator that the tool positioning devices 79 and 81 are not in close proximity. The feedback force control block 122 is then ended.

In response to the feedback signal from the master apparatus 64 to produce the haptic force, the control unit 92 presents a haptic force to the arms 94, 96, 98, to impede movement of the handle 102, and in the embodiment shown, the magnitude of haptic force is set depending on the degree of overlap by which the calculated distance between any two points on the left and right tool positioning devices 79 and 81 and the end effectors 71 and 73 is less than the threshold distance. In response to the feedback signal from the master apparatus 64 to cease producing haptic force, the control unit 92 ceases to present a haptic force to the arms 94, 96, 98, thus allowing movement of the handle 102.

Motion Control Block

The motion control block 120 shown in FIG. 6 includes codes that direct the master apparatus 64 to produce the slave control signals, in response to the configuration variables. The motion control block 120 uses the configuration variables produced by the kinematics block 118 to produce control wire length values by applying transfer functions to the calculated configuration variables to determine required wire lengths. Such transfer functions can be derived theoretically and/or empirically, for example, for the specific tools used. The motion control block 120 is also responsive to the "new" signal provided by the end effector position and orientation calculator block 116 of FIG. 6 and controlled by blocks 215 and 163 of FIG. 8.

Referring to FIG. 8, an active "new" signal is produced by block 215 of the end effector position and orientation calculation block 116 when the enablement signal is active and causes the present control wire length values to be represented by the slave control signals. An inactive "new" signal is produced by block 163, when the enablement signal is not active and when the enablement signal is active but the alignment error is not less than the threshold, and causes the previous control wire length values to be represented by the slave control signals.

CONCLUSION

The above described system is a robotic control system comprising a master apparatus 64 in communication with a plurality of input devices 58 and 60 having respective handles 102 and 105 capable of translational and rotational movement and a slave subsystem having a tool positioning device 79 and 81 corresponding to each respective handle, each tool positioning device 79 and 81 holding a respective tool 66 and 67 having an end effector 71 and 73 whose position and orientation is determined in response to a position and orientation of the respective corresponding handle.

The master apparatus 64 contains at least one processor circuit, the at least one processor circuit configured by the blocks shown in FIGS. 6-8 and 10 to cause the at least one processor to execute a method of operating the robotic control system to detect potential collisions between any of the tool positioning devices 79 and 81 and their respective end effectors 71 and 73, which may be part of the slave subsystem 54. In the embodiments shown, there are two tool positioning devices 79 and 81 and respectively, two end effectors 71 and 73, it being understood that there may be more than two tool positioning devices and end effectors in other embodiments.

In general the method involves causing the at least one processor circuit associated with the master apparatus 64 to produce desired new end effector positions and desired new end effector orientations of the respective end effectors 71 and 73, in response to current positions $\vec{F}_{MCURR}$ and current orientations $R_{MCURR}$ of corresponding respective handles 102 and 105. The at least one processor circuit is caused to use the desired new end effector positions and orientations $\vec{F}_{EENEW}$ and $R_{EENEW}$ to determine the pose of the tool positioning devices 79 and 81 and from there, calculate the distances from each point of a first plurality of points along the first tool positioning device 79 to each point of a plurality of points along at least one other tool positioning device 81. The at least one processor circuit is then caused to determine whether any of the calculated distances meets a proximity criterion and to notify the operator when the proximity criterion has been met.

Causing the at least one processor circuit to notify the operator tool positioning devices 79 and 81 meets a proximity criterion may include causing the at least one processor circuit to signal the input devices 58 and 60 associated with the handles 102 associated with the tool positioning devices 79 and 81, to cause the handles 102 associated with the tool positioning devices 79 and 81 associated with the calculated distance that meets the proximity criterion to present haptic feedback to the operator, the haptic feedback impeding movement of the handles in a direction that would shorten the calculated distance between the tool positioning devices 79 and 81 that meets the proximity criterion.

Alternatively or in addition, causing the at least one processor circuit to notify the operator may include causing the at least one processor circuit to produce annunciation signals for causing an annunciator to annunciate that the proximity criterion has been met and this may involve causing the at least one processor circuit to produce display control signals for causing the LCD display 68 to depict a visual representation indicative of the distance that meets the proximity criterion and/or causing the at least one processor circuit to produce audio control signals for causing an audio device to provide an audible sound indicative of the distance that meets the proximity criterion.

In the embodiments described, the at least one processor circuit may be configured to cause the input devices 58 to cease producing haptic feedback, to produce annunciation signals to cause an annunciator to cease to annunciate that a proximity criterion has been met, or to enable movement of the tool positioning devices 79 and 81 associated with the distance that met the proximity criterion when the calculated distance no longer meets the proximity criterion.

In the further alternative or in further addition, the at least one processor circuit may be configured to then disable movement of all tool positioning devices 79 and 81 associated with a distance that meets the proximity criterion.

Causing the at least one processor circuit to disable movement of all tool positioning devices 79 and 81 associated with the any distance that meets the proximity criterion may involve causing the at least one processor circuit to transmit control signals to respective slave subsystems 54 associated with the tool positioning devices 79 and 81 associated with the calculated distance that meets the proximity criterion, each control signal identifying a current end effector position and orientation based on a current position and orientation of the corresponding handle when the proximity criterion is not met and causing the at least one processor circuit to cause the control signals transmitted to the slave subsystems 54 associated with the tool positioning devices 79 and 81 associated with the calculated distance that meets the proximity criterion to identify a previous position ($\vec{F}_{EEBASE}$) and orientation ($R_{EEBASE}$) of associated respective end effectors 71 and 73 when the proximity criterion is met.

Producing the desired new end effector position and desired new end effector orientation and may involve causing the at least one processor circuit to receive from each input device 58 and 60 current handle position signals ($\vec{F}_{MCURR}$) and current handle orientation signals ($R_{MCURR}$) representing a current position and a current orientation respectively of the handle 102 of the corresponding input devices and causing the at least one processor circuit to produce, for corresponding tool positioning devices 79 and 81, new end effector position signals ($\vec{F}_{EENEW}$) and new end effector orientation signals ($R_{EENEW}$) defining the desired new end effector position and the desired new end effector orientation, respectively of the end effectors 71 and 73, in response to the corresponding current handle position signals ($\vec{F}_{MCURR}$) and the current handle orientation signals ($R_{MCURR}$).

Causing the at least one processor circuit to receive the current handle position signals $\vec{F}_{MCURR}$ and the current handle orientation signals $R_{MCURR}$ may involve causing the at least one processor circuit to periodically receive the current handle position signals and the current handle orientation signals.

The method may further involve causing the at least one processor circuit to receive an enablement signal controlled by the operator and causing the at least one processor circuit to detect a change in state of the enablement signal. When the change is detected the at least one processor may be caused to store the current handle position signals ($\vec{F}_{MCURR}$) and the current handle orientation signals ($R_{MCURR}$) as master base position signals ($\vec{F}_{MBAS}$) and master base orientation signals ($R_{MBASE}$) respectively; and store the new end effector position signals ($\vec{F}_{EENEW}$) and the new end effector orientation signals ($R_{EENEW}$) as end effector base position signals ($\vec{F}_{EEBASE}$) and end effector base orientation signals ($R_{EEBASE}$) respectively.

Causing the master apparatus 64 to produce the new end effector position signals ($\vec{F}_{EENEW}$) and the new end effector orientation signals ($R_{EENEW}$) may involve causing the master apparatus 64 to compute the new end effector position signals and the new end effector orientation signals according to the following relations:

$$\vec{F}_{EENEW} = A(\vec{F}_{MCURR} - \vec{F}_{MBAS}) + \vec{F}_{EEBASE}; \text{ and} \qquad (1a)$$

$$R_{EENEW} = R_{EEBASE} R_{MBASE}^{-1} R_{MCURR} \qquad (1b)$$

Each of the tool positioning devices 79 and 81 may include a plurality of segments 130 and 132 each comprised of a plurality of vertebrae 224 and at least some of the points in each of the plurality of points may be points on a respective segment or vertebrae of a segment 130 and 132.

The method may involve, for each tool positioning device 79 and 81, causing the at least one processor circuit to compute vectors from a reference point associated with the tool positioning devices 79 and 81 to a point on a segment of the tool positioning device, based on the desired new end effector position and orientation calculated for the end effector associated with the tool positioning device.

The method may further involve causing the at least one processor circuit to compute a position of at least one vertebrae associated with the segment, based on the position of the point on the segment.

While specific embodiments of the invention have been described and illustrated, such embodiments should be considered illustrative of the invention only and not as limiting the invention as construed in accordance with the accompanying claims.

What is claimed is:

1. A method of operating a robotic control system comprising a master apparatus in communication with a plurality of input devices including respective handles capable of translational and rotational movement and a slave system including a tool positioning device corresponding to each respective handle, each tool positioning device holding a respective tool including an end effector whose position and orientation is determined in response to a position and an orientation of the corresponding handle, the method comprising:

by at least one processor circuit associated with the master apparatus, producing desired new end effector positions and desired new end effector orientations of the respective end effectors in response to current positions and current orientations of the corresponding respective handles;

by the at least one processor circuit, determining a plurality of distances from each point of a first plurality of points along a first tool positioning device to each point of a plurality of points along at least one other tool positioning device using the desired new end effector positions and the desired new end effector orientations;

by the at least one processor circuit, determining that any of the distances meets a proximity criterion;

by the at least one processor circuit, generating notification signals for notifying an operator of the handles associated with respective tool positioning devices that one or more of the plurality of distances meets the proximity criterion;

by the at least one processor circuit, generating control signals for disabling movement of all tool positioning devices associated with the one or more of the plurality of distances that meets the proximity criterion; and by the at least one processor circuit, causing transmission of the control signals to respective slave systems associated with the tool positioning devices, each of the control signals identifying a previous position and a previous orientation of the respective end effectors when the proximity criterion is met and each of the control signals identifying a current end effector position and a current end effector orientation based on a current position and a current orientation of the corresponding handle when the proximity criterion is not met.

2. A non-transitory computer readable medium encoded with codes for directing a processor circuit to execute the method of claim 1.

3. An apparatus for use in a robotic control system, the apparatus in communication with a plurality of input devices including respective handles capable of translational and rotational movement and the robotic control system comprising a slave system including a tool positioning device corresponding to each respective handle, each tool positioning device holding a respective tool including an end effector whose position and orientation is determined in response to a position and an orientation of the corresponding handle, the apparatus comprising:

means for producing desired new end effector positions and desired new end effector orientations of the respective end effectors in response to current positions and current orientations of the corresponding respective handles;

means for determining a plurality of distances from each point of a first plurality of points along a first tool positioning device to each point of a plurality of points along at least one other tool positioning device based on the desired new end effector positions and desired new end effector orientations;

means for determining that any of the plurality of distances meets a proximity criterion;

means for generating notification signals for notifying an operator of the handles associated with respective tool positioning devices that one or more of the plurality of distances meets the proximity criterion;

means for generating control signals for disabling movement of all tool positioning devices associated with the one or more of the plurality of distances that meets the proximity criterion; and means for causing transmission of the control signals to respective slave systems associated with the tool positioning devices, each of the control signals identifying a previous position and a previous orientation of the respective end effectors when the proximity criterion is met and each of the control signals identifying a current end effector position and a current end effector orientation based on a current position and a current orientation of the corresponding handle when the proximity criterion is not met.

4. The apparatus of claim 3 wherein each of the tool positioning devices includes a plurality of segments, each of the plurality of segments comprised of a plurality of vertebrae and wherein at least some of the points in each of the plurality of points of the respective tool positioning device are points on a respective segment or a vertebrae of a segment.

5. The apparatus of claim 4 further comprising means for computing vectors to points along each tool positioning device from a reference point associated with the tool positioning device to a point on a segment of the plurality of segments of the tool positioning device based on the desired new end effector position and orientation calculated for the end effector associated with the tool positioning device.

6. The apparatus of claim 5 further comprising means for computing a position of at least one vertebrae associated with the segment based on the position of the point on the segment.

7. An apparatus for use in a robotic control system, the apparatus in communication with a plurality of input devices including respective handles capable of translational and rotational movement and a slave system including a tool positioning device corresponding to each respective handle, each tool positioning device holding a respective tool including an end effector whose position and orientation is determined in response to a position and an orientation of the corresponding handle, the apparatus comprising at least one processor circuit configured to:

produce desired new end effector positions and desired new end effector orientations of the respective end effectors in response to current positions and current orientations of the corresponding respective handles;

using the desired new end effector positions and the desired new end effector orientations, determine a plurality of distances from each point of a first plurality of points along a first tool positioning device to each point of a plurality of points along at least one other tool positioning device;

determine that any of the plurality of distances meets a proximity criterion;

generate notification signals for notifying an operator of the handles associated with respective tool positioning devices that one or more of the plurality of distances meets the proximity criterion;

generate control signals for disabling movement of all tool positioning devices associated with the one or more of the plurality of distances that meets the proximity criterion; and cause transmission of the control signals to respective slave systems associated with the tool positioning devices, each of the control signals identifying a previous position and a previous orientation of the respective end effectors when the proximity criterion is met and each of the control signals identifying a current end effector position and a current end effector orientation based on a current position and a current orientation of the corresponding handle when the proximity criterion is not met.

8. The apparatus of claim 7 wherein the at least one processor circuit is further configured to generate signals for causing the handles associated with the tool positioning devices associated with the one or more of the plurality of distances that meets the proximity criterion to present haptic feedback to the operator, the haptic feedback impeding movement of the handles in a direction that would shorten the one or more of the plurality of distances that meets the proximity criterion.

9. The apparatus of claim 7, wherein the at least one processor circuit is configured to generate notification signals for notifying the operator by producing annunciation signals for causing an annunciator to annunciate that the proximity criterion has been met.

10. The apparatus of claim 9 wherein the annunciation signals include display control signals for causing a display to depict a visual representation indicative of the one or more of the plurality of distances that meets the proximity criterion.

11. The apparatus of claim 9 wherein the annunciation signals include audio control signals for causing an audio device to provide an audible sound indicative of the one or more of the plurality of distances that meets the proximity criterion.

12. The apparatus of claim 7 wherein the at least one processor circuit is further configured to generate signals for enabling movement of the tool positioning devices associated with the one or more of the plurality of distances that meet the proximity criterion when the proximity criterion is no longer met.

13. The apparatus of claim 7 wherein the at least one processor circuit is configured to produce the desired new end effector position and the desired new end effector orientation by:

receiving from each input device current handle position signals ($\vec{P}_{MCURR}$) and current handle orientation signals ($R_{MCURR}$) representing a current position and a current orientation respectively of the handle of the corresponding input device; and producing, for corresponding tool positioning devices, new end effector position signals ($\vec{P}_{EENEW}$) and new end effector orientation signals ($R_{EENEW}$) defining the desired new end effector position and the desired new end effector orientation, respectively, of the end effector in response to the corresponding current handle position signals ($\vec{P}_{MCURR}$) and the current handle orientation signals ($R_{MCURR}$).

14. The apparatus of claim 13 wherein the at least one processor circuit is configured to periodically receive the current handle position signals and the current handle orientation signals.

15. The apparatus of claim 7 wherein the at least one processor circuit is configured to receive an enablement signal controlled by the operator and to detect a change in state of the enablement signal, and wherein, in response to the change being detected, the processor circuit is further configured to:

store the current handle position signals ($\vec{P}_{MCURR}$) and the current handle orientation signals ($R_{MCURR}$) as master base position signals ($\vec{P}_{MBAS}$) and master base orientation signals ($R_{MBASE}$) respectively; and store the new end effector position signals ($\vec{P}_{EENEW}$) and the new end effector orientation signals ($R_{EENEW}$) as end effector base position signals ($\vec{P}_{EEBASE}$) and end effector base orientation signals ($R_{EEBASE}$) respectively.

16. The apparatus of claim 15 wherein the at least one processor circuit is configured to compute the new end effector position signals ($\vec{P}_{EENEW}$) and the new end effector orientation signals ($R_{EENEW}$) according to:

$$\vec{P}_{EENEW} = A(\vec{P}_{MCURR} - \vec{P}_{MBASE}) + \vec{P}_{EEBASE}; \text{ and}$$

$$R_{EENEW} = R_{EEBASE} R_{MBASE}^{-1} R_{MCURR},$$

wherein A is a scalar value representing a scaling factor in translational motion between a master system and the slave system.

17. The apparatus of claim 7 wherein each of the tool positioning devices includes a plurality of segments, each of the plurality of segments comprised of a plurality of vertebrae and wherein at least some of the points in each of the plurality of points of the respective tool positioning device are points on a respective segment or a vertebrae of a segment.

18. The apparatus of claim 17 wherein the at least one processor circuit is configured to, for each tool positioning device, compute vectors from a reference point associated with the tool positioning device to a point on a segment of the plurality of segments of the tool positioning device based on the desired end effector position calculated for the end effector associated with the tool positioning device.

19. The apparatus of claim 18 wherein the at least one processor circuit is configured to compute a position of at least one vertebrae associated with the segment based on the position of the point on the segment.

* * * * *

UNITED STATES PATENT AND TRADEMARK OFFICE
CERTIFICATE OF CORRECTION

PATENT NO. : 10,729,503 B2
APPLICATION NO. : 15/570286
DATED : August 4, 2020
INVENTOR(S) : Peter John Kenneth Cameron It is certified that error appears in the above-identified patent and that said Letters Patent is hereby corrected as shown below:

In the Specification

In Column 2, Line 51, delete "$(\vec{F}_{MCURR})$" and insert --$(\vec{P}_{MCURR})$--.

In Column 2, Line 57, delete "$\vec{F}_{EENEW}$" and insert --$\vec{P}_{EENEW}$--.

In Column 2, Line 61, delete "$(\vec{F}_{MCURR})$" and insert --$(\vec{P}_{MCURR})$--.

In Column 3, Line 6, delete "$(\vec{F}_{MCURR})$" and insert --$(\vec{P}_{MCURR})$--.

In Column 3, Line 7, delete "$(\vec{F}_{MBAS})$" and insert --$(\vec{P}_{MBAS})$--.

In Column 3, Line 9, delete "$(\vec{F}_{EENEW})$" and insert --$(\vec{P}_{EENEW})$--.

In Column 3, Line 11, delete "$(\vec{F}_{EEBASE})$" and insert --$(\vec{P}_{EEBASE})$--.

In Column 3, Line 14, delete "$(\vec{F}_{EENEW})$" and insert --$(\vec{P}_{EENEW})$--.

In Column 3, Line 19, delete "$\vec{F}_{EENEW} = A(\vec{F}_{MCURR} - \vec{F}_{MBAS}) + \vec{F}_{EEBASE};$" and insert --$\vec{P}_{EENEW} = A(\vec{P}_{MCURR} - \vec{P}_{MBAS}) + \vec{P}_{EEBASE};$--.

In Column 4, Line 45, delete "$(\vec{F}_{MCURR})$" and insert --$(\vec{P}_{MCURR})$--.

Signed and Sealed this
Twentieth Day of October, 2020

Andrei Iancu
*Director of the United States Patent and Trademark Office*

CERTIFICATE OF CORRECTION (continued)
U.S. Pat. No. 10,729,503 B2

In Column 4, Line 50, delete "$(\mathsf{F}_{EENEW})$" and insert --$(\vec{P}_{EENEW})$--.

In Column 4, Line 54, delete "$(\mathsf{F}_{MCURR})$" and insert --$(\vec{P}_{MCURR})$--.

In Column 4, Line 63, delete "$(\mathsf{F}_{MCURR})$" and insert --$(\vec{P}_{MCURR})$--.

In Column 4, Line 65, delete "$(\mathsf{F}_{MBAS})$" and insert --$(\vec{P}_{MBAS})$--.

In Column 5, Line 1, delete "$(\mathsf{F}_{EENEW})$" and insert --$(\vec{P}_{EENEW})$--.

In Column 5, Line 3, delete "$(\mathsf{F}_{EEBASE})$" and insert --$(\vec{P}_{EEBASE})$--.

In Column 5, Line 6, delete "$(\mathsf{F}_{EENEW})$" and insert --$(\vec{P}_{EENEW})$--.

In Column 5, Line 10, delete "$\vec{F}_{EENEW} = A(\vec{F}_{MCURR} - \vec{F}_{MBAS}) + \vec{F}_{EEBASE};$" and insert --$\vec{P}_{EENEW} = A(\vec{P}_{MCURR} - \vec{P}_{MBAS}) + \vec{P}_{EEBASE}$--.

In Column 6, Line 32, delete "$(\mathsf{F}_{MCURR})$" and insert --$(\vec{P}_{MCURR})$--.

In Column 6, Line 37 (Approx.), delete "$(\mathsf{F}_{EENEW})$" and insert --$(\vec{P}_{EENEW})$--.

In Column 6, Line 41 (Approx.), delete "$(\mathsf{F}_{MCURR})$" and insert --$(\vec{P}_{MCURR})$--.

In Column 6, Line 50 (Approx.), delete "$(\mathsf{F}_{MCURR})$" and insert --$(\vec{P}_{MCURR})$--.

In Column 6, Line 51, delete "$(\mathsf{F}_{MBAS})$" and insert --$(\vec{P}_{MBAS})$--.

In Column 6, Line 53, delete "$(\mathsf{F}_{EENEW})$" and insert --$(\vec{P}_{EENEW})$--.

In Column 6, Line 55 (Approx.), delete "$(\mathsf{F}_{EEBASE})$" and insert --$(\vec{P}_{EEBASE})$--.

In Column 6, Line 58 (Approx.), delete "$(\mathsf{F}_{EENEW})$" and insert --$(\vec{P}_{EENEW})$--.

In Column 6, Line 62 (Approx.), delete "$\vec{F}_{EENEW} = A(\vec{F}_{MCURR} - \vec{F}_{MBAS}) + \vec{F}_{EEBASE};$" and insert --$\vec{P}_{EENEW} = A(\vec{P}_{MCURR} - \vec{P}_{MBAS}) + \vec{P}_{EEBASE}$--.

CERTIFICATE OF CORRECTION (continued)
U.S. Pat. No. 10,729,503 B2

In Column 9, Line 42 (Approx.), delete "$\vec{F}_{MCURR}$" and insert --$(\vec{P}_{MCURR})$--.

In Column 9, Line 45, delete "$\vec{F}_{MCURR}$" and insert --$(\vec{P}_{MCURR})$--.

In Column 10, Line 5, delete "$\vec{F}_{MCURR}$" and insert --$(\vec{P}_{MCURR})$--.

In Column 10, Line 11 (Approx.), delete "$\vec{F}_{MCURR}$" and insert --$(\vec{P}_{MCURR})$--.

In Column 10, Line 45, delete "$\vec{F}_{MCURR}$" and insert --$\vec{P}_{MCURR}$--.

In Column 10, Line 47, delete "$\vec{F}_{EENEW}$" and insert --$\vec{P}_{EENEW}$--.

In Column 10, Line 49, delete "$\vec{F}_{EENEW}$" and insert --$\vec{P}_{EENEW}$--.

In Column 10, Line 59, delete "$Z_v$," and insert --$Z_V$--.

In Column 11, Line 58, delete "$\vec{F}_{EENEW}$" and insert --$\vec{P}_{EENEW}$--.

In Column 11, Line 60, delete "$\vec{F}_{MCURR}$" and insert --$\vec{P}_{MCURR}$--.

In Column 12, Line 2, delete "$\vec{F}_{EENEW}$" and insert --$\vec{P}_{EENEW}$--.

In Column 12, Line 53, delete "$\vec{F}_{MBASE}$" and insert --$\vec{P}_{MBASE}$--.

In Column 12, Line 58, delete "$\vec{F}_{MBASE}$" and insert --$\vec{P}_{MBASE}$--.

In Column 12, Line 59, delete "$\vec{F}_{MCURR}$" and insert --$\vec{P}_{MCURR}$--.

In Column 12, Line 65, delete "$\vec{F}_{MBASE} = \vec{F}_{MCURR}$" and insert --$\vec{P}_{MBASE} = \vec{P}_{MCURR}$--.

In Column 13, Line 5, delete "$\vec{F}_{MBASE}$" and insert --$\vec{P}_{MBASE}$--.

In Column 13, Line 13, delete "$\vec{F}_{MBASE}$" and insert --$\vec{P}_{MBASE}$--.

In Column 13, Line 15, delete "$\vec{F}_{MCURR}$" and insert --$\vec{P}_{MCURR}$--.

CERTIFICATE OF CORRECTION (continued)
U.S. Pat. No. 10,729,503 B2

In Column 13, Line 19, delete "$\bar{F}_{MCURR}$" and insert --$\vec{P}_{MCURR}$--.

In Column 13, Line 22, delete "$\bar{F}_{EENEW}$" and insert --$\vec{P}_{EENEW}$--.

In Column 13, Line 27, delete "$\bar{F}_{EEBASE}$" and insert --$\vec{P}_{EEBASE}$--.

In Column 13, Line 36, delete "$\bar{F}_{EEBASE}$" and insert --$\vec{P}_{EEBASE}$--.

In Column 13, Line 37, delete "$\bar{F}_{EENEW}$" and insert --$\vec{P}_{EENEW}$--.

In Column 13, Line 42, delete "$\bar{F}_{EENEW}$" and insert --$\vec{P}_{EENEW}$--.

In Column 13, Line 42, delete "$\bar{F}_{EEBASE}$" and insert --$\vec{P}_{EEBASE}$--.

In Column 13, Line 43, delete "$\bar{F}_{EENEW}$" and insert --$\vec{P}_{EENEW}$--.

In Column 13, Line 54 (Approx.), delete "$\bar{F}_{EEBASE} = \bar{F}_{EENEW}$" and insert --$\vec{P}_{EEBASE} = \vec{P}_{EENEW}$;--.

In Column 13, Line 61, delete "$\bar{F}_{EEBASE}$" and insert --$\vec{P}_{EEBASE}$--.

In Column 14, Line 1, delete "$\bar{F}_{EEBASE}$" and insert --$\vec{P}_{EEBASE}$--.

In Column 14, Line 2, delete "$\bar{F}_{EENEW}$" and insert --$\vec{P}_{EENEW}$--.

In Column 14, Line 9, delete "$\bar{F}_{EENEW}$" and insert --$\vec{P}_{EENEW}$--.

In Column 14, Line 12, delete "$\bar{F}_{MCURR}$" and insert --$\vec{P}_{MCURR}$--.

In Column 14, Line 20, delete "$\bar{F}_{MCURR}$" and insert --$\vec{P}_{MCURR}$--.

In Column 14, Line 21, delete "$R_{MCURR}As$" and insert --$R_{MCURR}.As$--.

In Column 14, Line 22, delete "$\bar{F}_{MCURR}$" and insert --$\vec{P}_{MCURR}$--.

In Column 14, Line 25, delete "$\bar{F}_{MCURR}$" and insert --$\vec{P}_{MCURR}$--.

In Column 14, Line 27, delete "$\bar{F}_{MCURR}$" and insert --$\vec{P}_{MCURR}$--.

CERTIFICATE OF CORRECTION (continued)
U.S. Pat. No. 10,729,503 B2

In Column 14, Line 30, delete "$\bar{F}_{EENEW}$" and insert --$\vec{P}_{EENEW}$--.

In Column 14, Line 36, delete "$\bar{F}_{EENEW}$" and insert --$\vec{P}_{EENEW}$--.

In Column 14, Line 39, delete "$\bar{F}_{EENEW}$" and insert --$\vec{P}_{EENEW}$--.

In Column 14, Line 42, delete "$\bar{F}_{EENEW} = A(\bar{F}_{MCURR} - \bar{F}_{MBASE}) + \bar{F}_{EEBASE}$" and insert --$\vec{P}_{EENEW} = A(\vec{P}_{MCURR} - \vec{P}_{MBASE}) + \vec{P}_{EEBASE}$--.

In Column 14, Line 48, delete "$\bar{F}_{EENEW}$" and insert --$\vec{P}_{EENEW}$--.

In Column 14, Line 54, delete "$\bar{F}_{MCURR}$" and insert --$\vec{P}_{MCURR}$--.

In Column 14, Line 58, delete "$\bar{F}_{MBASE}$" and insert --$\vec{P}_{MBASE}$--.

In Column 14, Line 58, delete "$\bar{F}_{MCURR}$" and insert --$\vec{P}_{MCURR}$--.

In Column 14, Line 64, delete "$\bar{F}_{EEBASE}$" and insert --$\vec{P}_{EEBASE}$--.

In Column 14, Line 64, delete "$\bar{F}_{EENEW}$" and insert --$\vec{P}_{EENEW}$--.

In Column 15, Line 21, delete "applicant's U.S. applications" and insert --applicant's co-pending applications U.S.--.

In Column 15, Line 32, delete "$\bar{F}_{EENEW}$" and insert --$\vec{P}_{EENEW}$--.

In Column 15, Line 38, delete "$\bar{F}_{EEPREV}$" and insert --$\vec{P}_{EEPREV}$--.

In Column 15, Line 40, delete "$\bar{F}_{EENEW}$" and insert --$\vec{P}_{EENEW}$--.

In Column 15, Line 45, delete "$\bar{F}_{MCURR}$" and insert --$\vec{P}_{MCURR}$--.

In Column 15, Line 49, delete "$\bar{F}_{EENEW}$" and insert --$\vec{P}_{EENEW}$--.

In Column 15, Line 52, delete "$\bar{F}_{EENEW}$" and insert --$\vec{P}_{EENEW}$--.

In Column 15, Line 54, delete "$\bar{F}_{EEPREV}$" and insert --$\vec{P}_{EEPREV}$--.

CERTIFICATE OF CORRECTION (continued)
U.S. Pat. No. 10,729,503 B2

In Column 15, Line 56, delete "$\bar{F}_{EENEW}$" and insert --$\vec{P}_{EENEW}$--.

In Column 15, Line 59, delete "$\bar{F}_{EEPREV}$" and insert --$\vec{P}_{EEPREV}$--.

In Column 15, Line 61, delete "$\bar{F}_{EENEW}$" and insert --$\vec{P}_{EENEW}$--.

In Column 15, Line 63, delete "$\bar{F}_{MCURR}$" and insert --$\vec{P}_{MCURR}$--.

In Column 15, Line 66, delete "$\bar{F}_{EEPREV}$" and insert --$\vec{P}_{EEPREV}$--.

In Column 16, Line 11 (Approx.), delete "$\bar{F}_{EEPREV}$" and insert --$\vec{P}_{EEPREV}$--.

In Column 16, Line 14 (Approx.), delete "$\bar{F}_{EENEW}$" and insert --$\vec{P}_{EENEW}$--.

In Column 16, Line 22, delete "$\bar{F}_{EEPREV}$" and insert --$\vec{P}_{EEPREV}$--.

In Column 16, Line 27, delete "$\bar{F}_{EENEW}$" and insert --$\vec{P}_{EENEW}$--.

In Column 16, Line 40, delete "$\bar{F}_{EENEW}$" and insert --$\vec{P}_{EENEW}$--.

In Column 16, Line 42, delete "$\bar{F}_{EENEW}$" and insert --$\vec{P}_{EENEW}$--.

In Column 16, Line 46, delete "$\bar{F}_{EENEW}$" and insert --$\vec{P}_{EENEW}$--.

In Column 16, Line 51, delete "$\bar{F}_{EENEW}$" and insert --$\vec{P}_{EENEW}$--.

In Column 16, Line 56, delete "$\bar{F}_{EENEW}$" and insert --$\vec{P}_{EENEW}$--.

In Column 16, Line 61, delete "$\bar{F}_{EENEW}$" and insert --$\vec{P}_{EENEW}$--.

In Column 16, Line 66, delete "$\bar{F}_{EENEW}$" and insert --$\vec{P}_{EENEW}$--.

In Column 17, Line 12, delete "$x_v, y_v, z_v$," and insert --$X_V; Y_V; Z_V$.--.

In Column 18, Line 41, delete "$X_v$-$Y_v$," and insert --$X_V - Y_V$--.

In Column 19, Line 3, delete "$Y_v$," and insert --$X_V,$--.

In Column 19, Line 26, delete "$\vec{F}_{EENEW}$" and insert --$\vec{P}_{EENEW}$--.

In Column 19, Line 32 (Approx.), delete "$\bar{p}_{4/3} \cdot \bar{l} = \frac{-L_2 \cos \delta_{dist}(\sin \theta_{dist} - 1)}{\frac{\pi}{2} - \theta_{dist}} \bar{p}_{4/3} \cdot \bar{l} = \frac{-L_2 \cos \delta_2(\sin(\theta_2) - 1)}{\frac{\pi}{2} - \theta_2}$" and insert --$\bar{p}_{4/3} \cdot \bar{l} = \frac{-L_2 \cos \delta_{dist}(\sin \theta_{dist} - 1)}{\frac{\pi}{2} - \theta_{dist}} \bar{p}_{4/3} \cdot \bar{l} = \frac{-L_2 \cos \delta_2(\sin(\theta_2) - 1)}{\frac{\pi}{2} - \theta_2}$--.

In Column 19, Line 55, delete "$(\vec{F}_{3/v})$" and insert --$(\vec{P}_{3/V})$--.

In Column 20, Line 25, delete "f($\theta_{prox}$)=-0." and insert --f($\theta_{prox}$) = 0--.

In Column 20, Line 47, delete "n" and insert --in--.

In Column 20, Line 55, delete "$\vec{F}_{EENEW}$" and insert --$\vec{P}_{EENEW}$--.

In Column 21, Line 59, delete "$(\vec{F}_{1/v})$" and insert --$(\vec{P}_{1/V})$--.

In Column 22, Line 15, delete "$(\vec{F}_{1/v})$" and insert --$(\vec{P}_{1/V})$--.

In Column 22, Line 30, delete "$(\vec{F}_{2/v})$" and insert --$(\vec{P}_{2/V})$--.

In Column 22, Line 44, delete "$\theta_m$," and insert --$\theta_{prox}$--.

In Column 22, Line 55, delete "$(\vec{F}_{2/v})$" and insert --$(\vec{P}_{2/V})$--.

In Column 22, Line 66, delete "$(\vec{F}_{3/v})$" and insert --$(\vec{P}_{3/V})$--.

In Column 23, Line 32, delete "$(\vec{F}_{3/v})$" and insert --$(\vec{P}_{3/V})$--.

In Column 23, Line 41, delete "$(\vec{F}_{4/3})$" and insert --$(\vec{P}_{4/3})$--.

In Column 23, Line 45, delete "$\bar{p}_{4/3} \cdot \bar{l} = \frac{-L_2 \cos \delta_{dist}(\sin \theta_{dist} - 1)}{\frac{\pi}{2} - \theta_{dist}} \bar{p}_{4/3} \cdot \bar{l} = \frac{-L_2 \cos \delta_2(\sin(\theta_2) - 1)}{\frac{\pi}{2} - \theta_2}$" and insert --$\bar{p}_{4/3} \cdot \bar{l} = \frac{-L_2 \cos \delta_{dist}(\sin \theta_{dist} - 1)}{\frac{\pi}{2} - \theta_{dist}} \bar{p}_{4/3} \cdot \bar{l} = \frac{-L_2 \cos \delta_2(\sin(\theta_2) - 1)}{\frac{\pi}{2} - \theta_2}$--.

In Column 23, Line 57, delete "$(\vec{F}_{4/3})$" and insert --$(\vec{P}_{4/3})$--.

CERTIFICATE OF CORRECTION (continued)
U.S. Pat. No. 10,729,503 B2

In Column 23, Line 59, delete "$(\vec{F}_{3/V})$" and insert --$(\vec{P}_{3/V})$--.

In Column 23, Line 65, delete "$(\vec{F}_{5/4})$" and insert --$(\vec{P}_{5/4})$--.

In Column 24, Line 60, delete "$\vec{F}_{EENEW}$" and insert --$\vec{P}_{EENEW}$--.

In Column 25, Line 55, delete "embodiment;" and insert --embodiment,--.

In Column 27, Line 26, delete "$\vec{F}_{MCURR}$" and insert --$\vec{P}_{MCURR}$--.

In Column 27, Line 30, delete "$\vec{F}_{EENEW}$" and insert --$\vec{P}_{EENEW}$--.

In Column 28, Line 24, delete "$(\vec{F}_{EEBASE})$" and insert --$(\vec{P}_{EEBASE})$--.

In Column 28, Line 31, delete "$\vec{F}_{MCURR})$" and insert --$\vec{P}_{MCURR})$--.

In Column 28, Line 36, delete "$\vec{F}_{EENEW}$" and insert --$\vec{P}_{EENEW}$--.

In Column 28, Line 41, delete "$(\vec{F}_{MCURR})$" and insert --$(\vec{P}_{MCURR})$--.

In Column 28, Line 44, delete "$\vec{F}_{MCURR}$" and insert --$\vec{P}_{MCURR}$--.

In Column 28, Line 54, delete "$(\vec{F}_{MCURR})$" and insert --$(\vec{P}_{MCURR})$--.

In Column 28, Line 56, delete "$(\vec{F}_{MBAS})$" and insert --$(\vec{P}_{MBAS})$--.

In Column 28, Line 58, delete "$\vec{F}_{EENEW}$" and insert --$\vec{P}_{EENEW}$--.

In Column 28, Line 60, delete "$\vec{F}_{EEBASE}$" and insert --$\vec{P}_{EEBASE}$--.

In Column 28, Line 63, delete "$(\vec{F}_{EENEW})$" and insert --$(\vec{P}_{EENEW})$--.

In Column 29, Line 1, delete "$\vec{F}_{EENEW} = A(\vec{F}_{MCURR} - \vec{F}_{MBAS}) + \vec{F}_{EEBASE}$;" and insert --$\vec{P}_{EENEW} = A(\vec{P}_{MCURR} - \vec{P}_{MBAS}) + \vec{P}_{EEBASE}$--.

CERTIFICATE OF CORRECTION (continued)
U.S. Pat. No. 10,729,503 B2

In the Claims

In Column 31, Line 50, Claim 9, delete "7," and insert --7--.

In Column 32, Line 9, Claim 13, delete "$(\vec{F}_{MCURR})$" and insert --$(\vec{P}_{MCURR})$--.

In Column 32, Line 15 (Approx.), Claim 13, delete "$(\vec{F}_{EENEW})$" and insert --$(\vec{P}_{EENEW})$--.

In Column 32, Line 20 (Approx.), Claim 13, delete "$(\vec{F}_{MCURR})$" and insert --$(\vec{P}_{MCURR})$--.

In Column 32, Line 32 (Approx.), Claim 15, delete "$(\vec{F}_{MCURR})$" and insert --$(\vec{P}_{MCURR})$--.

In Column 32, Line 34 (Approx.), Claim 15, delete "$(\vec{F}_{MBAS})$" and insert --$(\vec{P}_{MBAS})$--.

In Column 32, Line 36 (Approx.), Claim 15, delete "$(\vec{F}_{EENEW})$" and insert --$(\vec{P}_{EENEW})$--.

In Column 32, Line 38 (Approx.), Claim 15, delete "$(\vec{F}_{EEBASE})$" and insert --$(\vec{P}_{EEBASE})$--.

In Column 32, Line 43 (Approx.), Claim 16, delete "$(\vec{F}_{EENEW})$" and insert --$(\vec{P}_{EENEW})$--.

In Column 32, Lines 46-49 (Approx.), Claim 16, delete "$\vec{P}_{EENEW} = A(\vec{P}_{MCURR} - \vec{P}_{MBASE}) + \vec{P}_{EEBASE}$; and $R_{EENEW} = R_{EEBASE} R_{MBASE}^{-1} R_{MCURR}$." and insert --$\vec{P}_{EENEW} = A(\vec{P}_{MCURR} - \vec{P}_{MBAS}) + \vec{P}_{EEBASE}$; and $R_{EENEW} = R_{EEBASE} R_{MBASE}^{-1} R_{MCURR}$,--.